US009693690B2

(12) United States Patent
Ater

(10) Patent No.: US 9,693,690 B2
(45) Date of Patent: Jul. 4, 2017

(54) DIGITAL ELECTRONIC FETAL HEART RATE AND UTERINE CONTRACTION MONITORING SYSTEM

(71) Applicant: Stewart Bruce Ater, Houston, TX (US)

(72) Inventor: Stewart Bruce Ater, Houston, TX (US)

( * ) Notice: Subject to any disclaimer, the term of this patent is extended or adjusted under 35 U.S.C. 154(b) by 0 days.

(21) Appl. No.: 15/071,979

(22) Filed: Mar. 16, 2016

(65) Prior Publication Data
US 2016/0270658 A1     Sep. 22, 2016

Related U.S. Application Data

(60) Provisional application No. 62/135,274, filed on Mar. 19, 2015.

(51) Int. Cl.
| | |
|---|---|
| *A61B 5/00* | (2006.01) |
| *A61B 5/024* | (2006.01) |
| *A61B 5/03* | (2006.01) |
| *A61B 8/02* | (2006.01) |
| *A61B 8/08* | (2006.01) |
| *A61M 5/172* | (2006.01) |

(52) U.S. Cl.
CPC ........ *A61B 5/0011* (2013.01); *A61B 5/02411* (2013.01); *A61B 5/02438* (2013.01); *A61B 5/033* (2013.01); *A61B 5/4356* (2013.01); *A61B 5/4839* (2013.01); *A61B 5/743* (2013.01); *A61B 5/746* (2013.01); *A61B 8/02* (2013.01); *A61B 8/0866* (2013.01); *A61M 5/1723* (2013.01)

(58) Field of Classification Search
CPC . A61B 5/0011; A61B 5/4356; A61B 5/02411; A61B 5/033; A61B 5/02438; A61B 8/02; A61B 8/0866; A61B 5/4839; A61B 5/743; A61B 5/746; A61M 5/1723
See application file for complete search history.

(56) References Cited

U.S. PATENT DOCUMENTS

| | | | | |
|---|---|---|---|---|
| 4,213,455 A | * | 7/1980 | Ellson | A61B 5/033 604/66 |
| 7,113,819 B2 | | 9/2006 | Hamilton et al. | |

(Continued)

FOREIGN PATENT DOCUMENTS

EP     1852065 A1     7/2007

*Primary Examiner* — Katherine Fernandez
*Assistant Examiner* — Colin T Sakamoto
(74) *Attorney, Agent, or Firm* — Rao DeBoer Osterrieder, PLLC

(57) ABSTRACT

A digital electronic fetal heart rate and uterine contraction monitoring system with an electronic fetal monitor, a contraction monitoring sensor and a fetal heart rate sensor. A controller configured to receive fetal heart rate data and uterine contraction pressure, identify a contraction start time and end time, and calculate each rest interval in seconds between contractions. The system compares rest intervals to a safe preset limit for rest intervals, calculates a median rest interval and an average rest interval for each fifteen-minute period of labor, and presents a contraction and rest interval graph to a display. The system can activate an alarm on an electronic fetal monitor display or a third party display and can pause a pump that is delivering a drug to increase uterine contractions when a significant criteria of excessive uterine activity is detected outside preset limits to assure adequate blood flow to the fetal brain.

22 Claims, 25 Drawing Sheets

(56) References Cited

U.S. PATENT DOCUMENTS

| | | |
|---|---|---|
| 2006/0204532 A1 | 9/2006 | John |
| 2006/0247942 A1 | 11/2006 | Payne et al. |
| 2009/0012432 A1 | 1/2009 | Sharf |
| 2010/0168528 A1 | 7/2010 | Evans |
| 2011/0192398 A1 | 8/2011 | Euliano et al. |
| 2012/0150010 A1 | 6/2012 | Hayes-Gill et al. |
| 2014/0039340 A1 | 2/2014 | Young |

\* cited by examiner

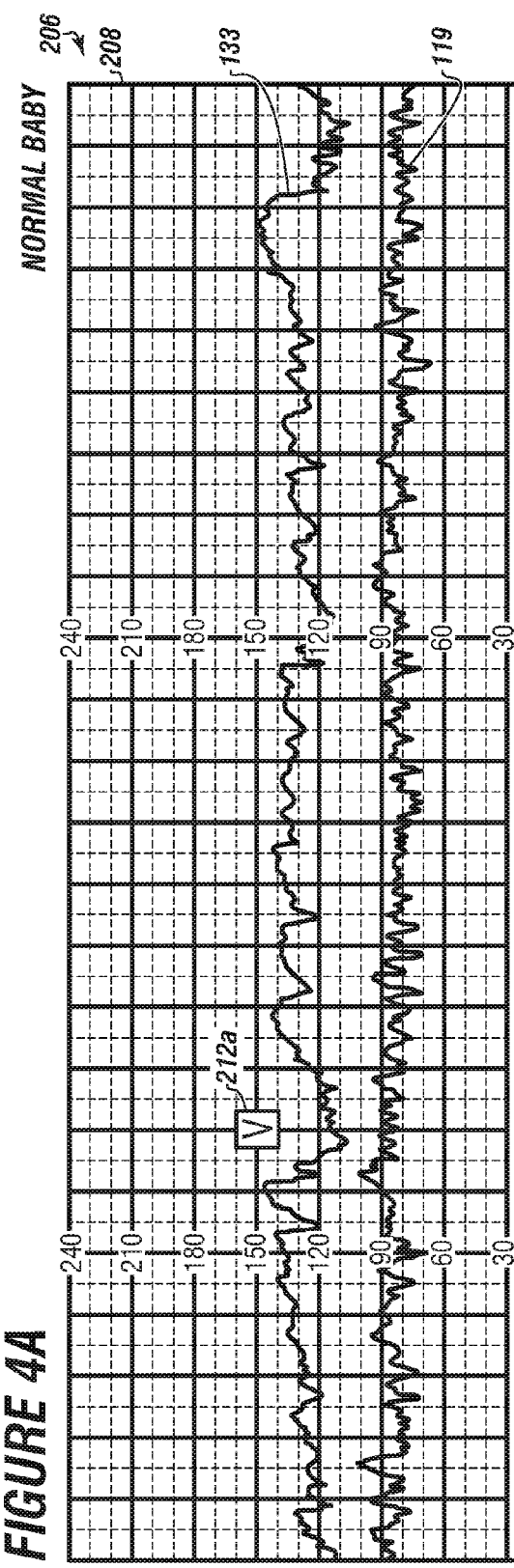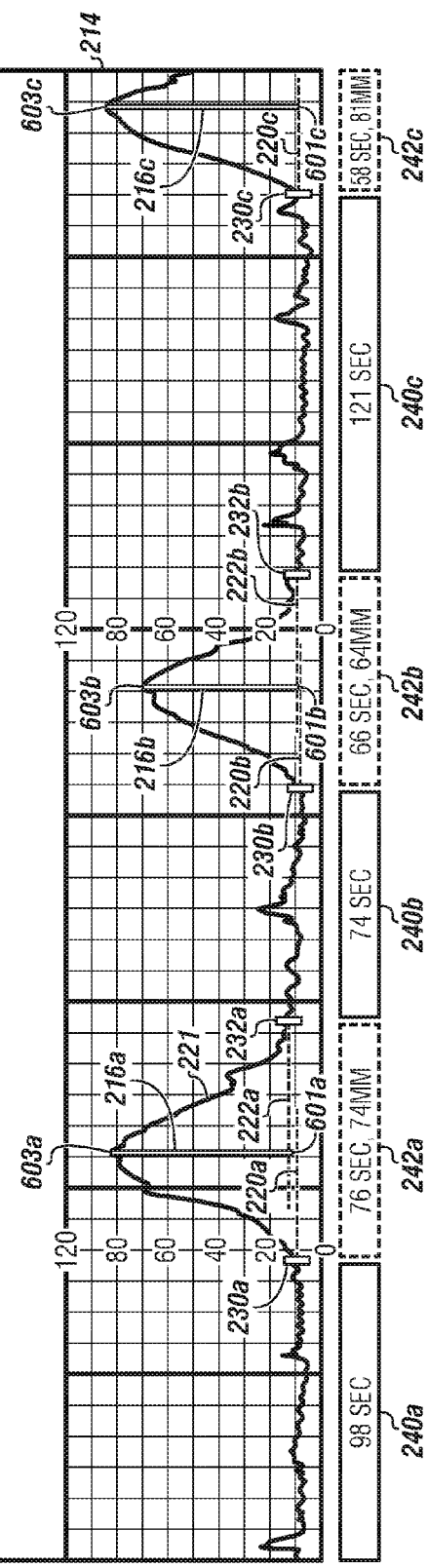
FIGURE 4A

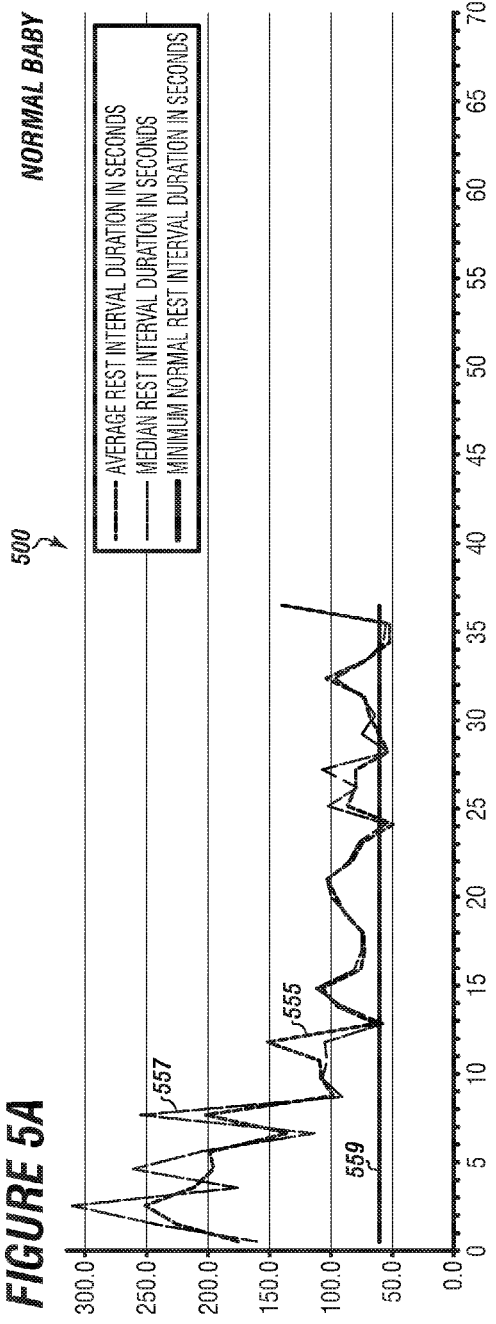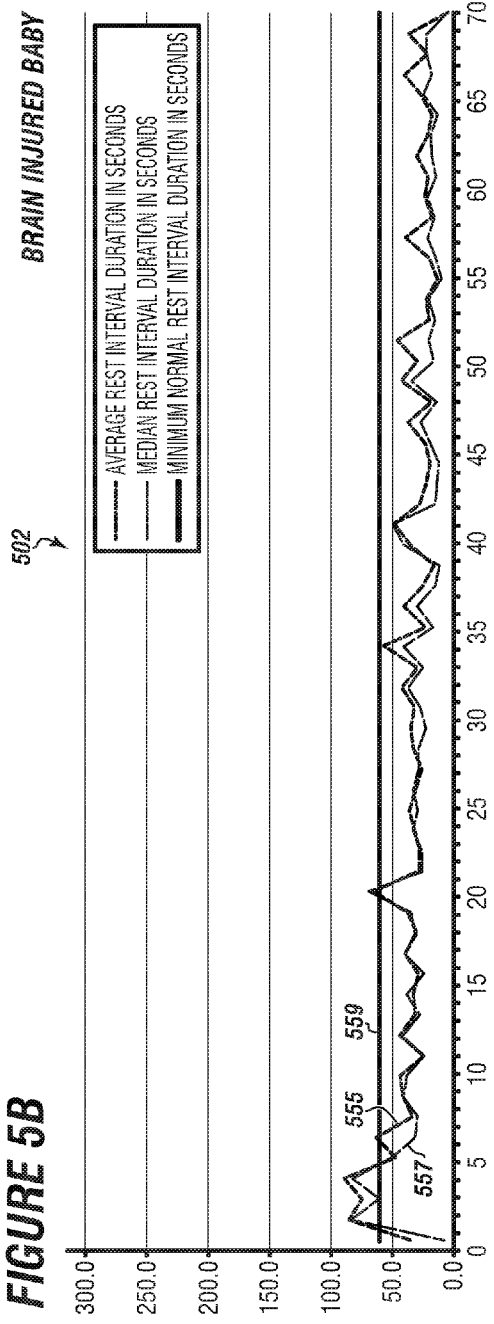

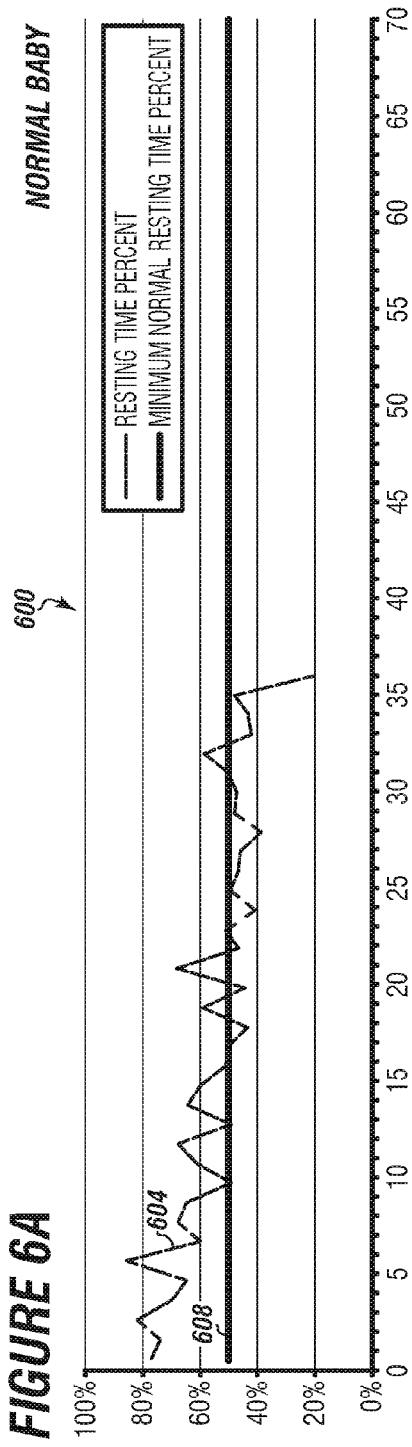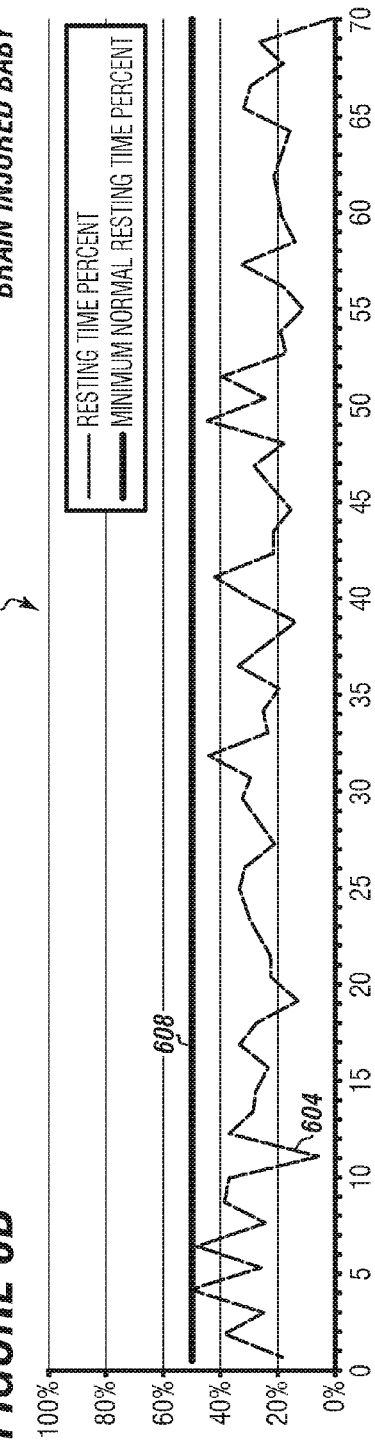

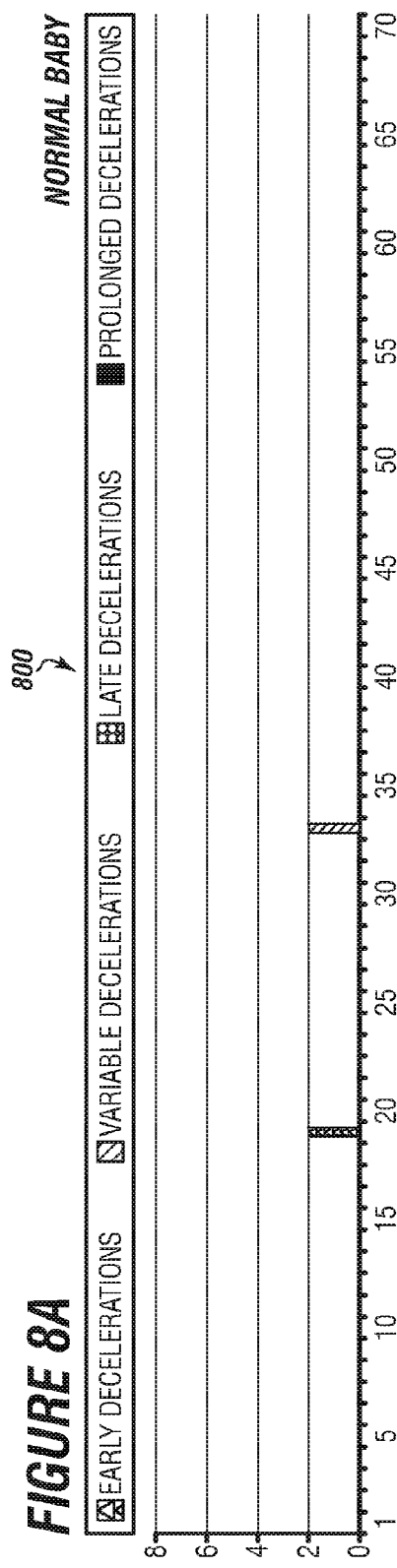
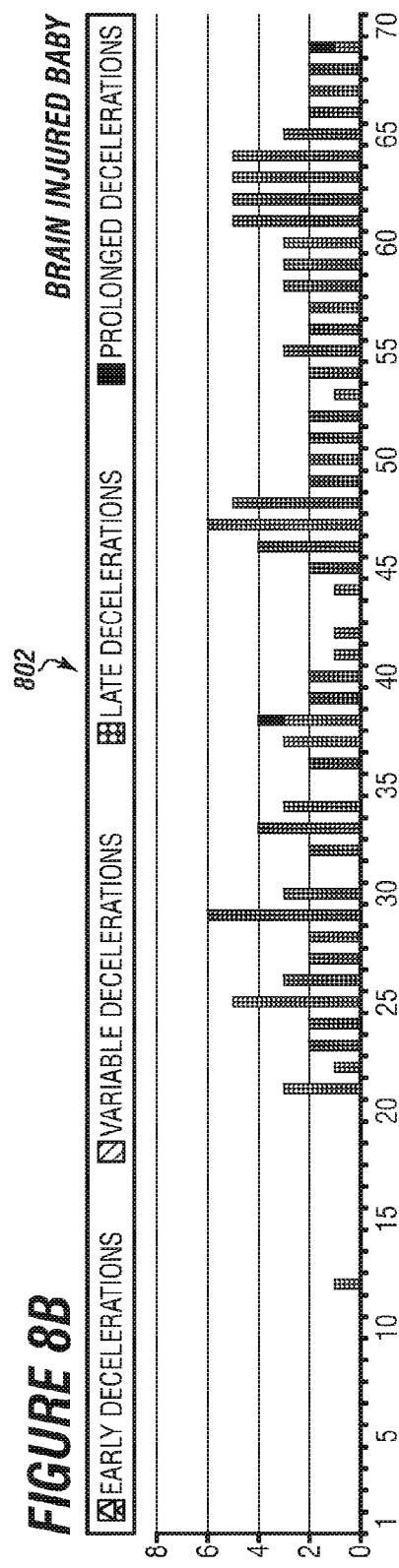

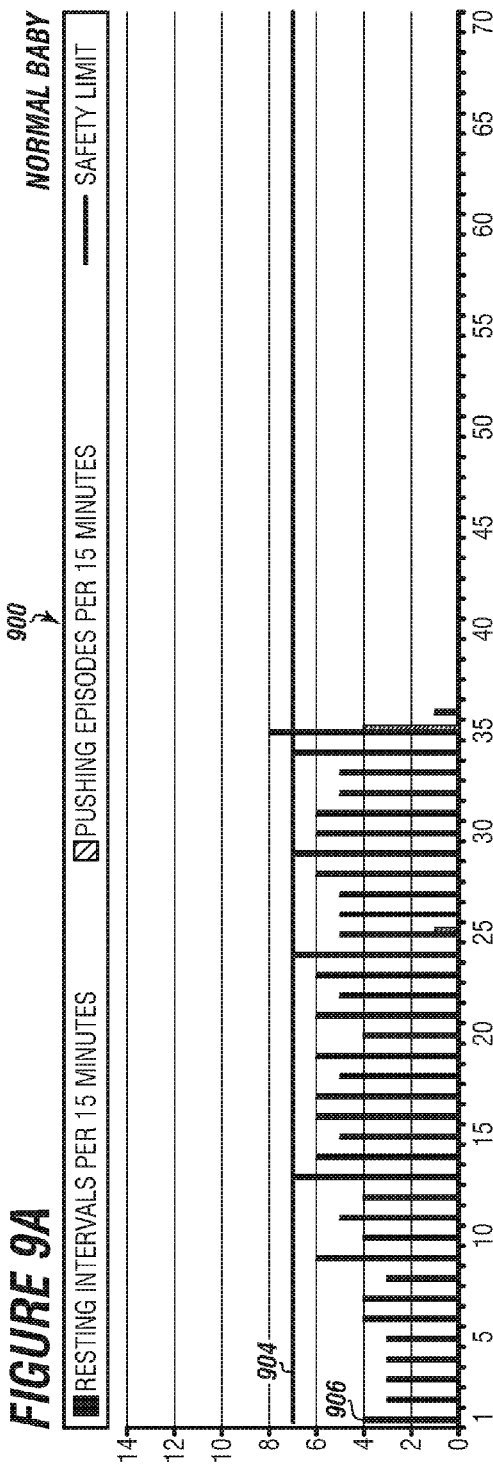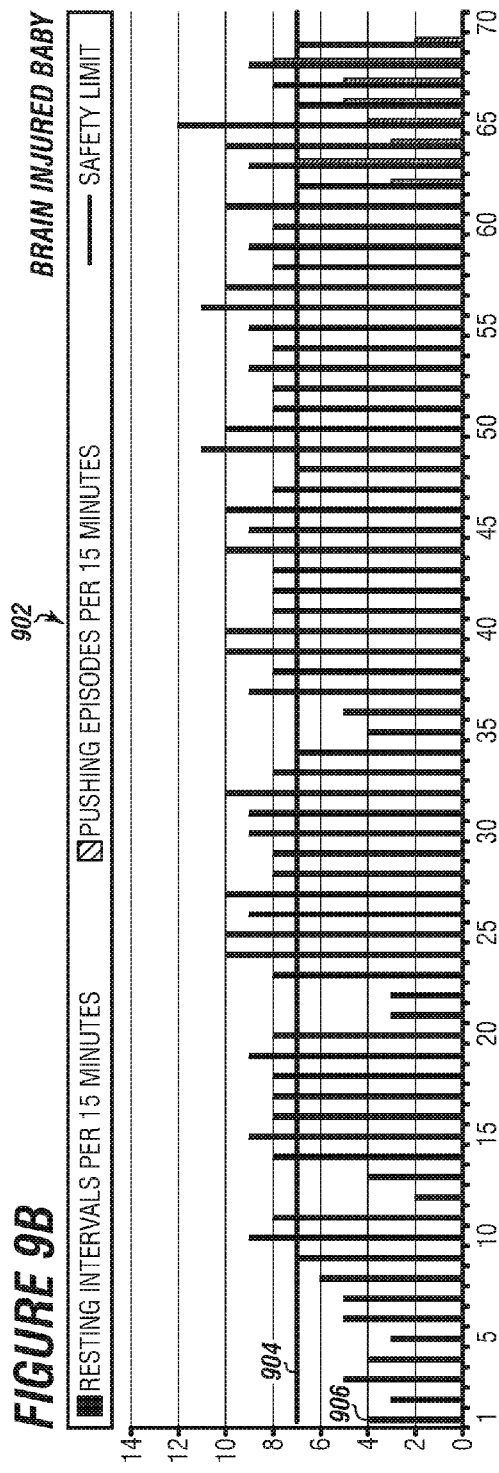

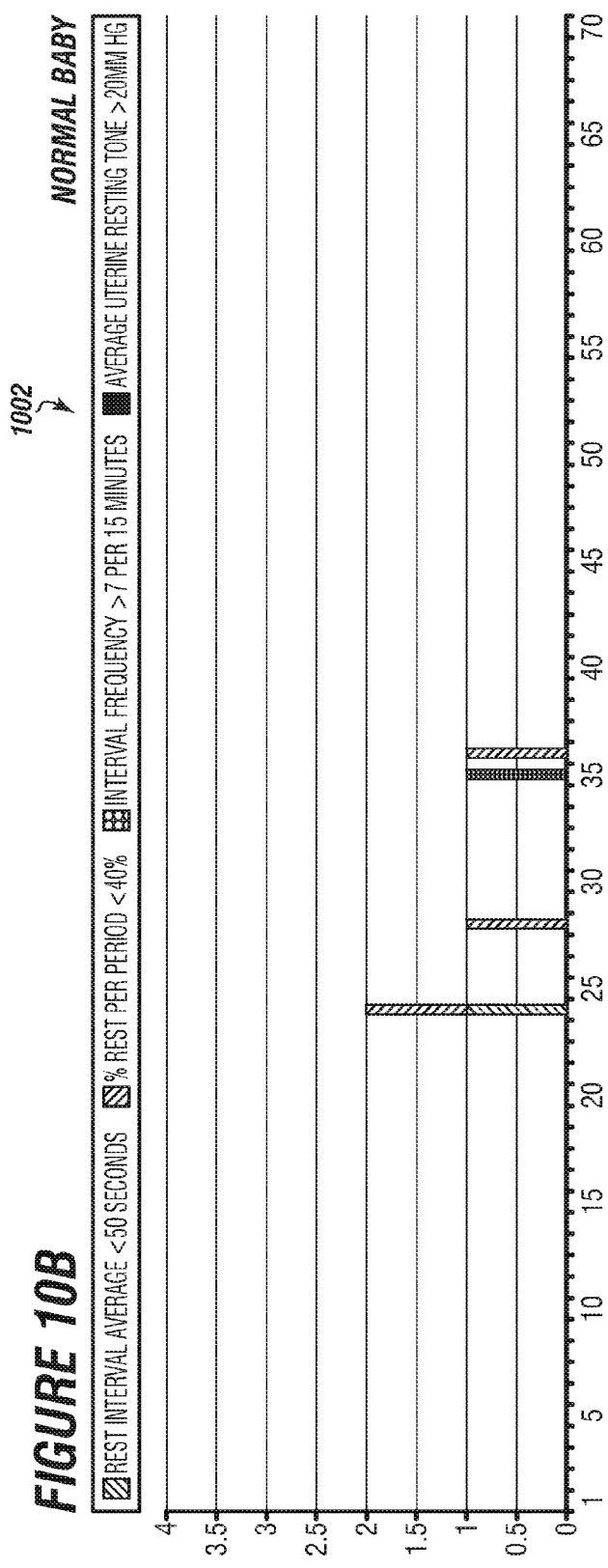

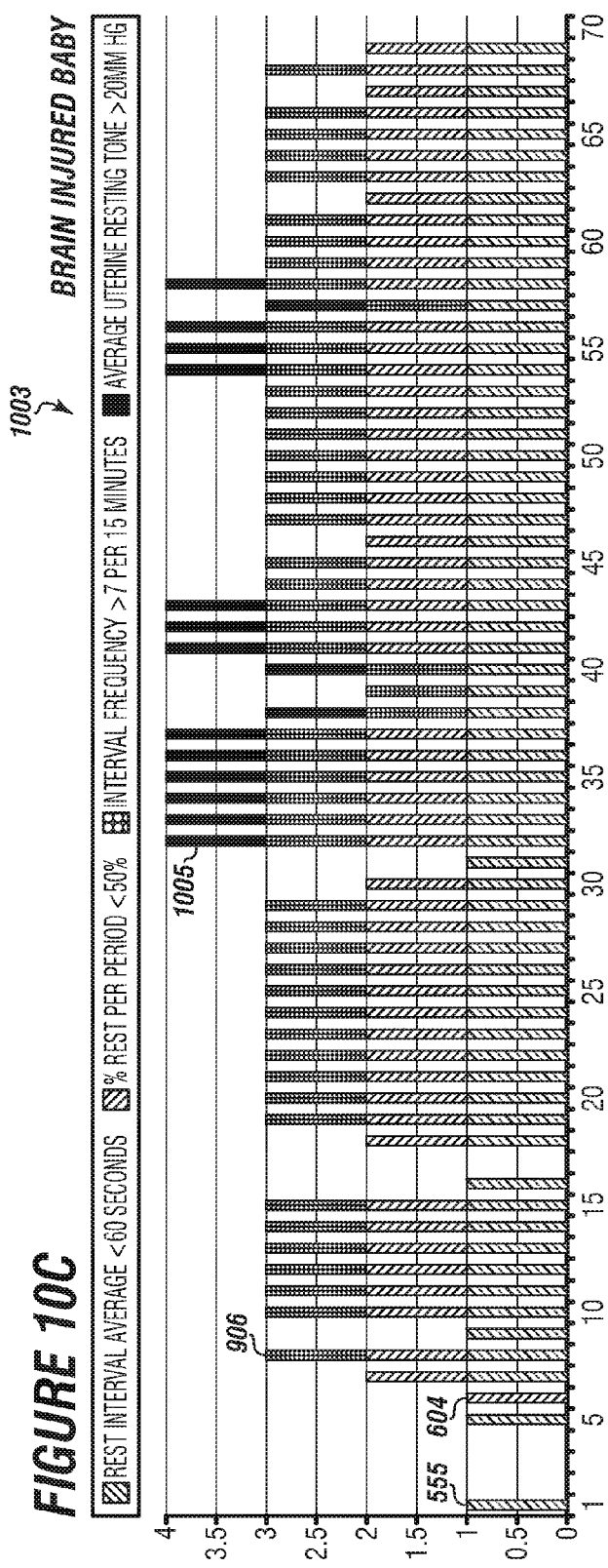

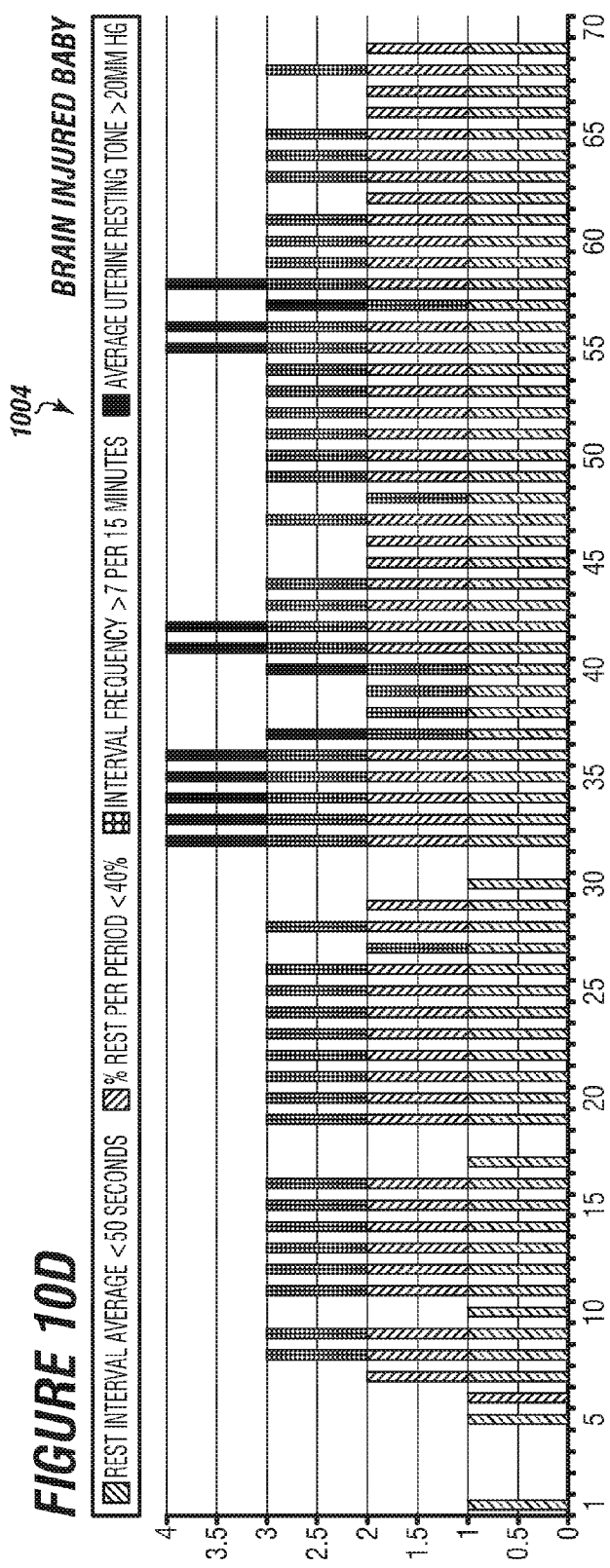

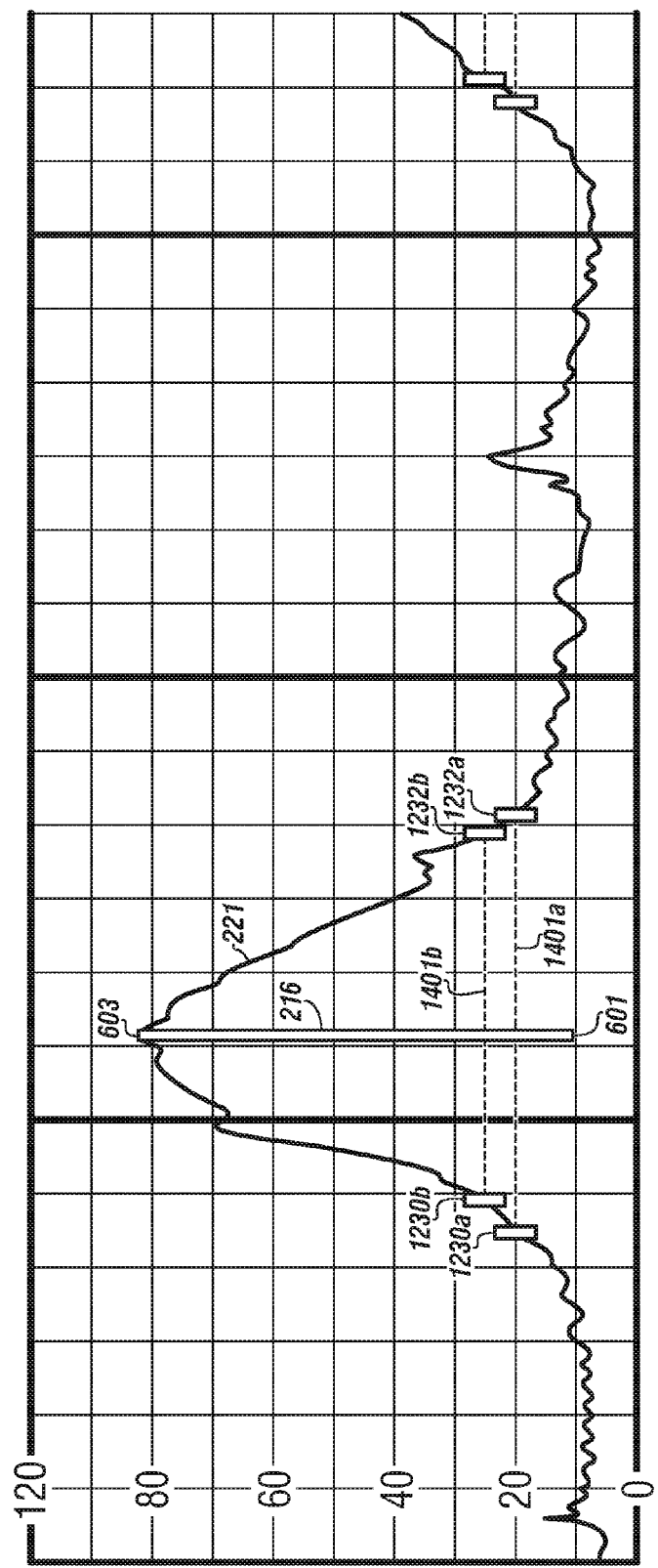

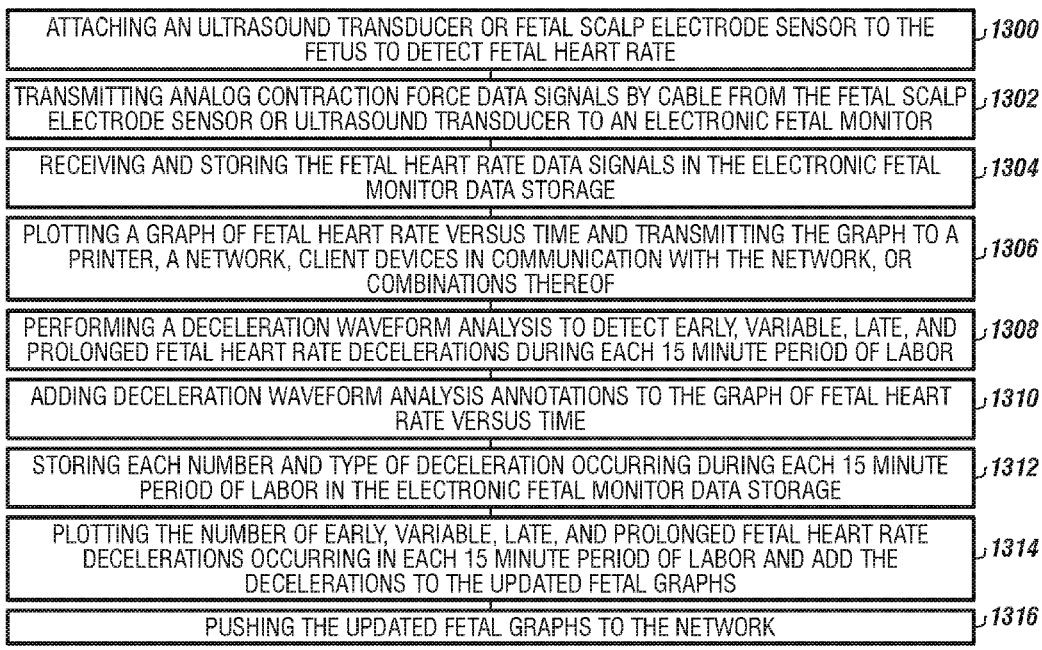

DIGITAL ELECTRONIC FETAL HEART RATE AND UTERINE CONTRACTION MONITORING SYSTEM

CROSS REFERENCE TO RELATED APPLICATIONS

The current application claims priority to and the benefit of U.S. Provisional Patent Application Ser. No. 62/135,274 filed on Mar. 19, 2015, entitled "Digital Electronic Fetal Heart Rate and Uterine Contraction Monitoring System". This reference is hereby incorporated in its entirety.

FIELD

The present embodiments generally relate to a digital electronic fetal heart rate and uterine contraction monitoring system.

BACKGROUND

A need exists for a device to protect the fetal brain against emerging risks of reduced fetal brain blood flow, known as ischemia, and reduced fetal oxygen, known as hypoxia, due to excessive uterine activity (XSUA).

A further need exists for a device to recognize when there is repetitively too little rest between contractions and when contractions occur too often, such as more than seven contractions during a fifteen-minute rest period of labor for a mother.

A need exists for an internet connected device to provide a discreet alarm message to a healthcare worker, such as a nurse or doctor, to a personal device, such as a cellular phone or a smart phone via a network or the internet.

A need exists for a device to automatically protect the fetal brain when potentially brain-injuring excessive uterine activity is detected by stopping a pump that infuses synthetic oxytocin to a mother to increase contractions.

A need exists for a risk mitigating device usable in hospitals that provides a digital record that labor has not been injurious, providing a visual display that reassures providers and expectant parents, which prevents unnecessary lawsuits against hospitals and doctors providing birthing care.

A need exists for a device to protect the fetal brain by providing data analysis and graphs that reveal potentially injurious trends of fetal heart rate and uterine contraction pressure to doctors and nurses during 8 to 15 minute segments of labor and by identifying risk trends that evaluate the combination of cumulative contraction pressure and contraction duration.

A need exists for a device to protect the fetal brain by computing and displaying accurate, continuously updated and easily-recognizable graphics that allow doctors and nurses to diagnose the important features and trends of potentially injurious excessive uterine activity throughout the entire course labor.

The American College of Obstetricians and Gynecologists recommended "*Development and evaluation of new technologies for intrapartum fetal monitoring to augment EFM interpretation and clinical decision making at the bedside*" as well as "*Exploration of computer interpretation of EFM as an aid, or even replacement, to visual interpretation*" in the Neonatal Encephalopathy and Neurologic Outcome, Second Edition, copyright 2014 as developed under the direction of the Task Force on Neonatal Encephalopathy.

The present embodiments meet these needs.

BRIEF DESCRIPTION OF THE DRAWINGS

The detailed description will be better understood in conjunction with the accompanying drawings as follows:

FIG. 4A depicts a fetal heart rate tracing and maternal heart rate tracing above a uterine contraction tracing during an eight-minute segment of labor for a normal baby.

FIG. 5A depicts a graph of labor for a normal baby showing durations of average and median rest intervals in seconds during each fifteen-minute period of labor and normal rest intervals that are used for comparison.

FIG. 5B depicts a graph of labor for a brain injured baby showing durations of average and median rest intervals in seconds during each fifteen-minute period of labor and normal rest intervals that are used for comparison.

FIG. 6A depicts a graph of resting time percent between contractions during each fifteen-minute period of labor as compared to a user adjustable minimum normal resting time percent used for comparison for a normal baby.

FIG. 6B depicts a graph of resting time percent between contractions during each fifteen-minute period of labor as compared to a user adjustable minimum normal resting time percent used for comparison for a brain injured baby.

FIG. 8A shows a graph of labor of a normal baby of fetal heart rate decelerations as detected by the system during each fifteen minute period of labor.

FIG. 8B shows a graph of labor of a brain injured baby of fetal heart rate decelerations as detected by the system during each fifteen minute period of labor.

FIG. 9A shows a graph of labor of a normal baby of the number of resting intervals and the number of pushing episodes during each fifteen-minute period of labor as detected by the system.

FIG. 9B shows a graph of labor of a brain injured baby of the number of resting intervals and the number of pushing episodes during each fifteen-minute period of labor as detected by the system.

FIG. 10B shows a graph of a normal baby's labor depicting occurrence of excessive uterine activity parameters defined by a decreased sensitivity definition of average rest interval duration (<50 seconds) and a decreased sensitivity definition of percent resting time (<40%).

FIG. 10C shows a graph of a brain injured a baby's labor depicting occurrence of excessive uterine activity parameters defined by an increased sensitivity definition of average rest interval duration (<60 seconds) and an increased sensitivity definition of resting time (<50%).

FIG. 10D shows a graph a brain injured baby's labor depicting occurrence of excessive uterine activity parameters defined by a reduced sensitivity definition of average rest interval duration (<50 seconds) and a reduced sensitive definition of resting time (<40%).

FIG. 14 depicts a graph using an optional method to determine duration of contractions when pressure exceeds user-selected minimum limits.

FIG. 16 depicts an exemplary sequence of steps according to the system as it relates to analysis of fetal heart rate decelerations.

Figure 1:
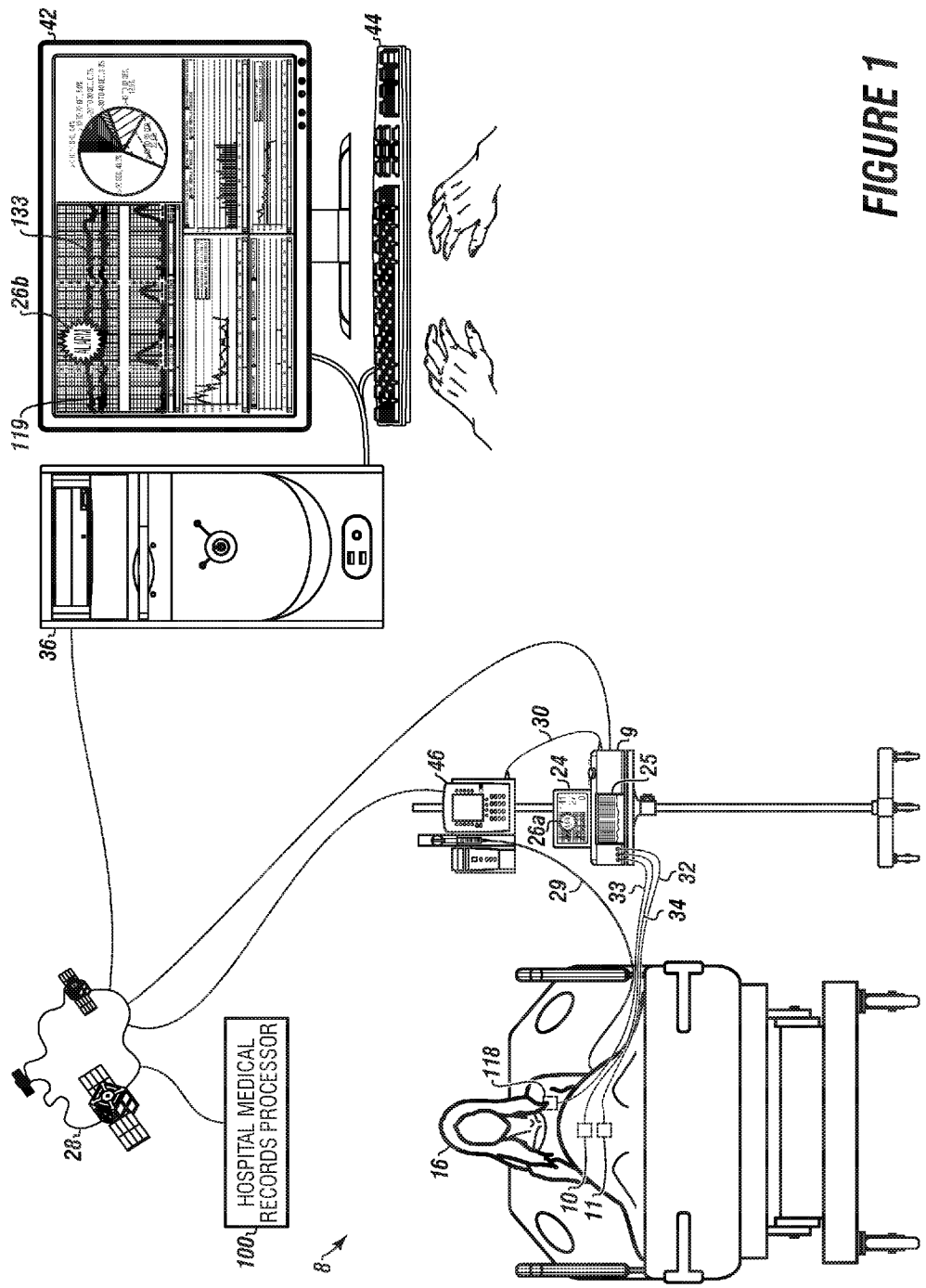
FIG. 1 is a diagram of an overview of a digital electronic fetal heart rate and material heart rate with uterine contraction monitoring system.

The present embodiments are detailed below with reference to the listed Figures.

DETAILED DESCRIPTION OF THE EMBODIMENTS

Before explaining the present apparatus and system in detail, it is to be understood that the apparatus and system is not limited to the particular embodiments and that it can be practiced or carried out in various ways.

The present embodiments generally relate to a digital electronic fetal heart rate and uterine contraction monitoring system.

A benefit of the invention is that the system can be used to protect the fetal brain against hypoxic ischemic encephalopathy as well as an emerging risk of reduced brain blood flow, known as ischemia, due to excessive uterine activity (XSUA).

A benefit of the invention is that the system can be used to protect the fetal brain by recognizing when there is repetitively too little rest between contractions and when contractions occur too often, such as more than seven contractions during a fifteen-minute rest period of labor for a mother.

A benefit of the invention is that the system can be used to protect the fetal brain by using an internet connected device to provide an alarm to a healthcare worker, such as a nurse or obstetrician, to a personal device, such as a cellular phone or smart phone.

A benefit of the invention is that digital electronic fetal heart rate and uterine contraction monitoring system can be used to protect the fetal brain by automatically and without human intervention to stop a pump that delivers a drug that increases contractions.

A benefit of the invention is that the digital electronic fetal heart rate and uterine contraction monitoring system, can be used in hospitals and other birthing centers to create a digital record that labor has not been injurious, providing a real time visual display that reassures providers and even expectant parents, which automatically provides a record to prevent unnecessary lawsuits against hospitals and doctors providing birthing care.

A benefit of the invention is that the digital electronic fetal heart rate and uterine contraction monitoring system can be used to protect the fetal brain by providing a graph of 8 to 15 minute segments of fetal heart rate and uterine contraction strength.

A benefit of the invention is that the system can be used to protect the fetal brain by displaying the entire history of the most important features of uterine activity with easily understood graphs.

The digital electronic fetal heart rate and uterine contraction monitoring system can be used to protect the fetal brain by presenting information to healthcare workers for each fifteen minute period of labor to demonstrate the adequacy of rest between uterine contractions, defined as the duration of time from the end or offset of a contraction to the beginning or onset of the next contraction,] including: (1) average rest between contractions, (2) median rest between contractions, (3) percentage of time resting between contractions, (4) number of rest periods between contractions, (5) number of rest intervals that are very reassuring (greater than 90 seconds), (6) number of rest intervals that are probably safe (from 60 to 90 seconds, (7) number of rest intervals that are suboptimal (from 40 to 60 seconds), (8) number of rest intervals that are potentially injurious (from 20 to 40 seconds), and number of rest intervals that are likely injurious if repetitive (from 1 to 20 seconds).

The digital fetal heart rate monitoring system can be used to analyze numerous aspects of excessive uterine activity to provide sensitive detection of potentially dangerous conditions that lead to fetal brain injuries, including hypoxic ischemic encephalopathy (HIE). The digital fetal heart rate and contraction monitoring system can be selective and configured to avoid over-alarming when an occasional rest interval is too short but overall trends are safe. The digital electronic fetal heart rate and uterine contraction monitoring system can allow user-defined fine tuning adjustments of default settings used to determine when to alarm and when to send alerts to nurses and obstetricians to prevent excessive contractions that can decrease oxygen delivery to a fetus (known as hypoxia). Prolonged hypoxia can cause fetal heart dysfunction and decreased fetal blood flow (known as ischemia). Excessive uterine activity, including excessive uterine contractions, not only may decrease oxygen delivery to the fetal brain, but may also decrease overall blood flow to the fetal brain. The invention can prevent such decreases in overall blood flow and oxygen delivery to a fetus by providing timely warning of these risks to healthcare workers, such as a nurses or obstetricians to allow timely interventions.

Additionally, the invention can reduce mechanical trauma to fetal head and brain and brain ischemia and bleeding due to mechanical trauma.

In embodiments, the digital electronic fetal heart rate and uterine contraction monitoring system can be used to display the labor curve, including cervical dilation and fetal head station, oxytocin (PITOCIN™) dosing history and additional features such as fetal heart rate abnormalities, including baseline rate, variability, and number of early, late, variable and prolonged decelerations during each period of labor. For very long labors, the graphic display of the entire labor may not all fit on one page of the display. In that case, the graphs can be scrolled left and right to allow users to see the data more clearly.

The invention will impact the cost of HIE and ischemic perinatal brain injuries of approximately $50 billion dollars per year to the American society by reducing cost.

The invention will reduce milder brain damage to a child, including but not limited to learning disabilities, autism, decreased cognitive and executive functions, and problems of emotional regulation and attention. Milder brain damage impairs independent living skills, intellectual ability, and ability to earn a living. The invention can prevent these problems when used appropriately.

Since the cause of excessive uterine activity is often the infusion of synthetic oxytocin to speed up labor to speed up labor by increasing uterine contraction frequency, duration, and strength, this infusion can cause uterine contractions to be too long and too strong with inadequate rest between contractions. Even without oxytocin administration, if the fetal head size is too large to fit a birth canal, problems can develop from increased pressures during labor exerted upon the fetal head. Increased pressures on the fetal head occur when labor lasts a longer period of time. The invention can prevent dystocia, which refers to excessively long periods of labor due to delay of cervical dilation and delay of descent of the fetal head through the birth canal.

The invention can identify more than seven uterine contractions per fifteen-minute period of labor, a known risk for hypoxic ischemic encephalopathy.

The invention can identify resting intervals between uterine contractions less than 60 seconds duration.

The invention can identify uterine resting tone between contractions that is stronger than 20 to 25 mm Hg.

The system can monitor, compare, and calculate median and average rest interval durations between contractions and other physiological parameters of excessive uterine activity.

The system can provide automatic continuous surveillance to detect excessive and potentially injurious uterine activity before it occurs long enough to cause permanent fetal brain damage.

The system can also provide automatic continuous surveillance to detect fetal heart rate decelerations.

The system can provide surveillance to detect dystocia by monitoring labor curve data, including rates of cervical dilatation and fetal head descent, and comparing this to preset norms.

The system can provide automatic alarms and discrete methods to relay information to doctors and nurses and medical providers for the mother whenever average and median rest intervals and other parameters exceed user adjustable preset safety limits.

The system can provide automatic alarms enabling medical providers to make treatment decisions and interrupt injurious conditions before brain injuries occur, such as discontinuing oxytocin infusion or deciding to perform a Cesarean section.

The system can provide automatic pausing of an oxytocin infusion pump to a mother until medical providers respond to detected elevated risks.

The system can provide automatic alarms allowing medical providers to adjust system settings for optimal balance of effective risk detection while minimizing alarm fatigue.

The system can provide a summary of risk events during labor and delivery and automatically produce a report for doctors and nurses who will care for the baby after birth to facilitate timely diagnosis and treatment of these risks.

The system can provide low pass filters that reject meaningless high frequency waveforms and artifacts that are not due to uterine contractions. Only contractions long enough and strong enough will be assessed as true contractions. The system can ignore contractions waveforms with contraction pressure less than a user-adjustable default of 30 mm Hg absolute contraction peak pressure measurement and user-adjustable active pressure less than a default of 10 mm Hg above uterine pressure baseline. In addition, the system can reject peaks on the contraction graph that lack significant contraction duration, such as a user-adjustable default duration less than 30 seconds.

The system can reject wave forms on the contraction graph that are due to fetal movements.

In an embodiment, the system can provide neural network signal processing to evaluate fetal heart rate decelerations.

In an embodiment, doctors and nurses can adjust the system's risk settings to provide customized balance for each mother's individual risk profiles.

The system can enable user-adjustments of safety limits, including resting interval duration, percent resting, contraction frequency, excessive average uterine resting tone, frequency of occurrence of four types of decelerations, rates of cervical dilatation and fetal head descent on the labor curve along with other medical and physical parameters, including temperature of the mother and heart rate of the mother.

In embodiments, the system can use color to display technical adequacy of heart rate and contraction input data for example, for example, the color green can indicate the data is good, yellow can indicate that technical problems exist with the monitoring and red can indicate signal loss.

In embodiments, the system can have a unit that electronically connects from a mother's room to an obstetrical management system with computer monitor with a color display. The system can electronically communicate with a fetal monitor and to the mother's heart rate monitor as well as a network, such as a global communication network or a local area network. The system can communicate to computers at a nurse's station as well as client devices of other medical providers, such as a physician. The client device can be a smart phone or a tablet computer of a physician, as an example.

In embodiments, a computer chip containing formulas on an EXCEL™ spreadsheet application, a MATLAB™ or other programming language program can be used to store the data, calculate risks and graph abnormal trends. The chip can work as an add on to existing electronic fetal monitoring equipment. The chip can be physically located in an add-on device or in the electronic fetal monitor itself, which can receive data from the electronic fetal monitor data ports. In embodiments, the chip can send output signals via wireless connectivity, such as BLUETOOTH™, to a network that can provide communication to a doctor's or nurse's computer or client device over a secure connection. In embodiments, the system can run as a smartphone application when connected to an input port that receives digital maternal and fetal heart rate data and contraction data.

In embodiments, the system can continuously send graphs, with a slight time delay for processing, of annotated fetal and maternal heart rate graphs versus time and contraction pressure versus time. These graphs for both normal babies and abnormal babies can provide graphic and numerical analysis of duration of each rest interval during labor and duration and pressure of each contraction.

In embodiments, the system can compute and transmit graphic and numerical information about the following trends simultaneously: (1) evidence of excessive uterine activity, (2) evidence of decelerations, (3) evidence of an abnormal labor curve with protraction, arrest or both protraction and arrest of cervical dilatation, fetal head descent or both cervical dilatation and fetal head descent or partogram, (4) evidence of high oxytocin infusion rate trends that correlate with excessive uterine activity and/or fetal deceleration trends, and (5) evidence of excessive number of periods with pushing.

The system can detect and warn of many risky conditions and technical problems with labor simultaneously, as examples, but not limited to: (a) inadequate or absent fetal heart rate, (b) inadequate or absent contraction signals, and (c) inadequate or absent maternal heart rate signal (i.e. either mother's heart stopped or transducer fell off mother).

The term "alarm" as used herein can refer to an audible alarm, a visual alarm, a text message, an email, and combinations thereof.

The term "average rest interval" as used herein can refer to a quotient obtained by dividing the sum total of a set of figures by the number of figures. This formula can compute the sum of each rest interval during a fifteen-minute period of labor and divides by the number of rest intervals in each period of labor.

The term "brackets" as used herein can refer to solid easily visible black lines, flashing bars, or red lines, or arrows which clearly denote the start and stop times of rest intervals between contractions.

The term "client device" as used herein can include portable devices, such as cellular phones, smart phones, laptops, computers, tablet computers, nursing station monitors, similar devices, and combinations thereof, which can bi-directionally communicate with the electronic fetal monitor.

The term "contraction duration annotations" as used herein can refer to annotations on adjacent tocographs that depict uterine contractions. Annotations can provide quantitative duration of uterine contractions measured in seconds displayed in dashed line boxes for a similar visual identifier below contractions that visually identify duration of contractions, which are displayed on graphs created by the system that present the contraction durations.

The term "contraction onset" as used herein can refer to a measure of uterine pressure, such as when pressure rises above a baseline and continues to rise to a discernable contraction peak.

The term "contraction offset" as used herein can refer to a measure of uterine pressure, such as when pressure decreases from an observable contraction peak and reaches a baseline in which pressure no longer decreases.

The term "contraction pressure annotations" as used herein can refer to annotations on adjacent tocographs that depict uterine contractions. Annotations can provide quantitative pressure measurements of uterine contractions measured in mm Hg displayed in dashed line boxes for a similar visual identifier below contractions that visually identify duration of contractions, which are displayed on graphs created by the system that present the contraction durations.

The term "controller" as used herein can refer to a chip for instructing a processor in an electronic fetal monitor or a remote processor, wherein the chip can contain a data storage or a processor with a data storage.

The term "data storage" as used herein refers to a non-transitory computer readable medium, such as a memory area on a chip, a hard disk drive, solid state drive, flash drive, tape drive, or a memory storage area which can contain data or computer instructions to instruct the processor to perform a specific function. The term "non-transitory computer readable medium" excludes any transitory signals but includes any non-transitory data storage circuitry, e.g., buffers, cache, and queues, within transceivers of transitory signals.

The term "deceleration annotations" as used herein can refer to letters that symbolize display annotations "E", "V", "L" or "P" to respectively denote early, variable, late or prolonged fetal heart rate decelerations that were detected by the system. In embodiments, the annotations can be displayed above detected deceleration waveforms on the fetal heart rate tracing.

The term "electronic fetal monitor" as used herein can refer to a technical means of recording (-graphy) the fetal heartbeat (cardio-) and the uterine contractions (toco-) during pregnancy, typically in the third trimester. The machine can be used to perform the monitoring is called a cardiotocograph, more commonly known as an electronic fetal monitor (EFM).

In embodiments, the electronic fetal monitor can be a device that acquires uterine contraction information via a tocotransducer. The electronic fetal monitor can acquire fetal heart rate information via an ultrasound transducer. In addition to the ultrasound that determines the fetal heart rate, an electrode can be attached to the mother's skin, typically on the abdomen or leg, to acquire maternal heart rate. Electrical signals can be sent via cables to ports on the bedside electronic fetal monitor.

The term "fetal scalp electrode" as used herein can refer to an internal fetal monitoring option that can be used after the mother's membranes are ruptured. A fetal scalp electrode can be attached to the fetal scalp. When it is used, the scalp electrode usually detects a more accurate fetal heart rate signal than the ultrasound transducer can produce. A fetal scalp electrode can be placed by screwing a tiny sire into the top layers of the baby's scalp, then relaying the baby's heart rate via an electrical cable to the electronic fetal monitor.

The term "intracranial ischemia" as used herein can refer to inadequate blood flow inside the fetal head.

The term "intrauterine pressure catheter" or "IUPC" as used herein can refer to a device placed into the amniotic space during labor in order to measure the strength of uterine contractions. An intrauterine pressure catheter (IUPC) can be used in conjunction with a pressure transducer during labor induction to measure the pressure created by contractions during labor and can detect accurate pressure measurements needed to determine contraction frequency, duration and strength. This internal monitoring option can be mainly used by a doctor or midwife who wants to determine the strength of uterine contractions under higher-risk situations. It provides more accurate information to determine whether excessive uterine activity is present and is particularly useful when stimulants of uterine contractions, such as oxytocin (PITOCIN™), are used.

The term "labor" as used herein can refer to childbirth, the process of delivering a baby and the placenta, membranes, and umbilical cord from the uterus to the vagina to the outside world.

The term "median rest interval" as used herein can refer to the value that represents the point at which there are as many instances above as there are below. The median rest interval duration can be computed by a statistical formula using system software. Essentially, the median rest interval in each period of labor can be chosen as the interval that is shorter than half the other intervals and longer than half the other intervals.

The term "network" as used herein can refer to a satellite network, a cellular network, the internet, another global communication network, a neural network, any network known in the industry, or combinations thereof.

The term "oxytocin" as used herein can refer to a mammalian neurohypophysial hormone. Produced by the hypothalamus and stored and secreted by the posterior pituitary gland, oxytocin acts primarily as a neuromodulator in the brain. During labor, oxytocin is the most potent stimulant of uterine contractions.

The term "pressure signals" as used herein can refer to signals, such as intrauterine pressure ranging from 0 to 100 millimeters of mercury.

The term "printer" as used herein can refer to any known printer, such as a paper printer, which can create a continuous strip of paper printing of the fetal heart rate graph above and uterine contraction graph below.

The term "processor" as used herein can refer to a computer, such as a laptop, a microprocessor, printed circuitry for processing, or similar device for processing data and producing results which can be transmitted.

The term "pump" as used herein can refer to an infusion pump that administers selectable dosage infusion rates of a premixed intravenous solution of oxytocin, such as PITOCIN™ to the mother via an intravenous line.

The term "rest interval" as used herein can refer to a time from a contraction end time (offset) to the subsequent contraction start time (onset).

The term "rest interval annotations" as used herein can refer to annotations on adjacent tocographs that depict uterine contractions. Annotations can provide quantitative duration of rest intervals, measured in seconds displayed in solid boxes for a similar visual identifier, below rest intervals that visually identify duration of rest intervals, which are displayed on graphs created by the system that present the contraction durations and rest intervals between contraction durations.

The term "safe preset limit for average rest interval duration" as used herein can refer to a unit of time, such as in seconds, which allows adequate time for safe placental and brain reperfusion between contractions. The safe preset limit for average rest interval duration can be set by a user, such as medical personnel in the labor room. A default safety preset limit for average rest interval duration can be 60 seconds.

The term "safe user defined limits of excessive uterine activity" as used herein can refer to activity that is not dangerous, wherein dangerous preset limit examples can include median and average rest interval <60 seconds, contraction frequency >7 per fifteen-minute period of labor, uterine resting tone >25 mm Hg (Hypertonus), contraction duration greater than 90 seconds, and <50% resting time percent between contractions during each period of labor.

The term "tocodynamometer or TOCO" as used herein can refer to an electronic device for monitoring and recording uterine contractions in labor. The tocodynamometer or TOCO can comprise a pressure transducer that is applied to the mother's abdomen by means of a belt to monitor pressure created by the underlying fundus of the uterus. The tocodynamometer can be connected to a machine that records the duration of the contractions and the resting interval between contractions. The relative pressure intensity of the contractions can also be measured by the tocodynamometer, but cannot be quantified in precise measurements of pressure. The tocodynamometer is a component of external monitoring in childbirth. In embodiments, the contraction monitoring sensor can be a tocodynamometer secured to the mother in labor, an intrauterine pressure catheter secured to the mother and connected to a pressure transducer to measure strength and duration of contractions for the mother in labor, or combinations thereof.

The term "ultrasound sensor" as used herein can refer to a device that acquires fetal heart rate information via an ultrasound transducer. In addition to the ultrasound that determines the fetal heart rate, an electrode can be attached to the mother's skin, typically on the abdomen or leg, to acquire maternal heart rate. Electrical signals can be sent via cables to ports on the bedside electronic fetal monitor (EFM).

Figure 2:
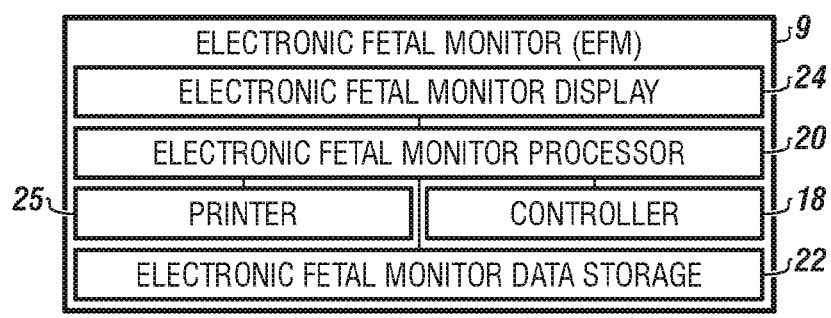
FIG. 2 is a diagram of an electronic fetal monitor according to one or more embodiments.
Figure 3A:
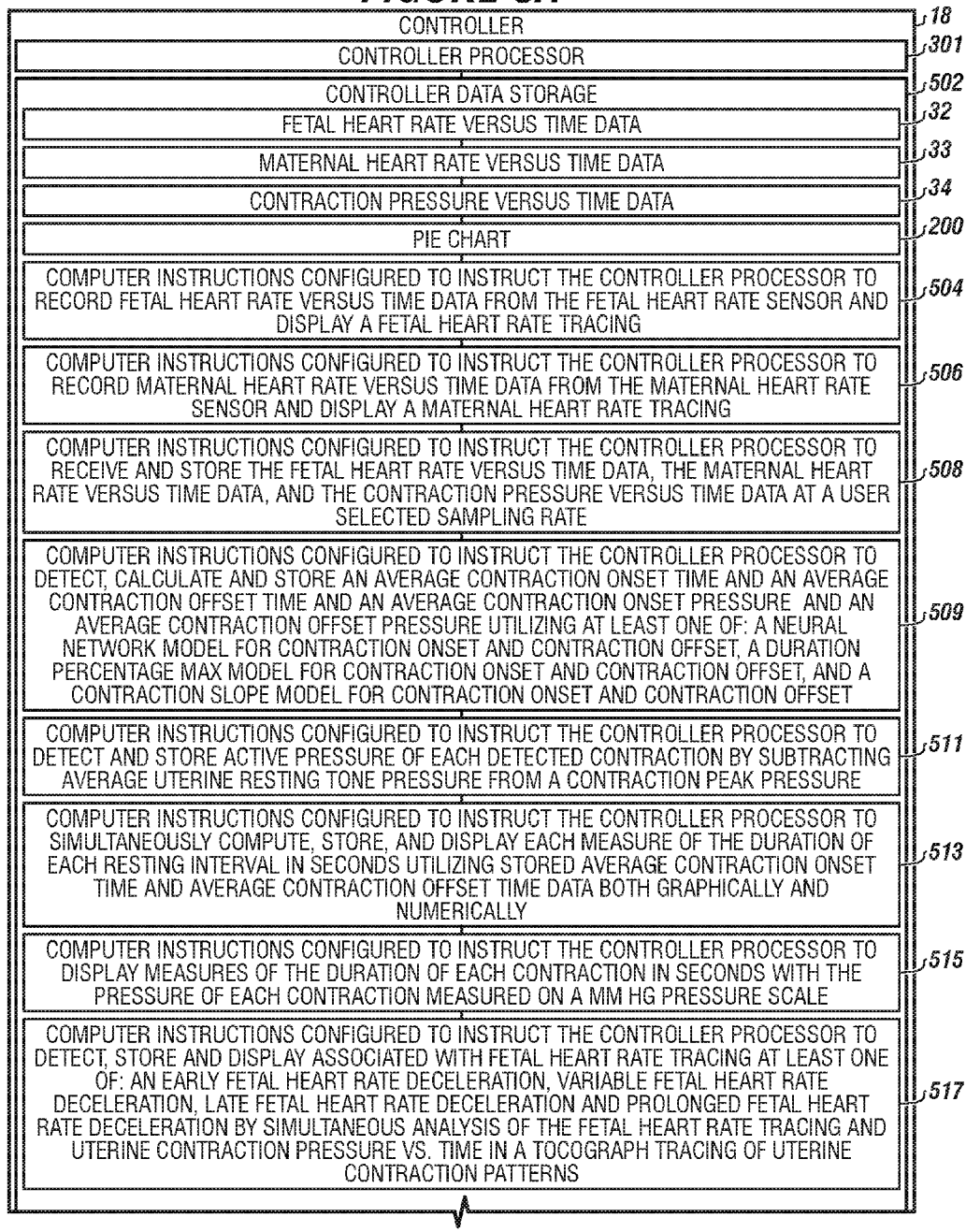
FIGS. 3A-3D depict the controller, controller processor, and data storage of the digital electronic fetal heart rate monitor.
Figure 3B:
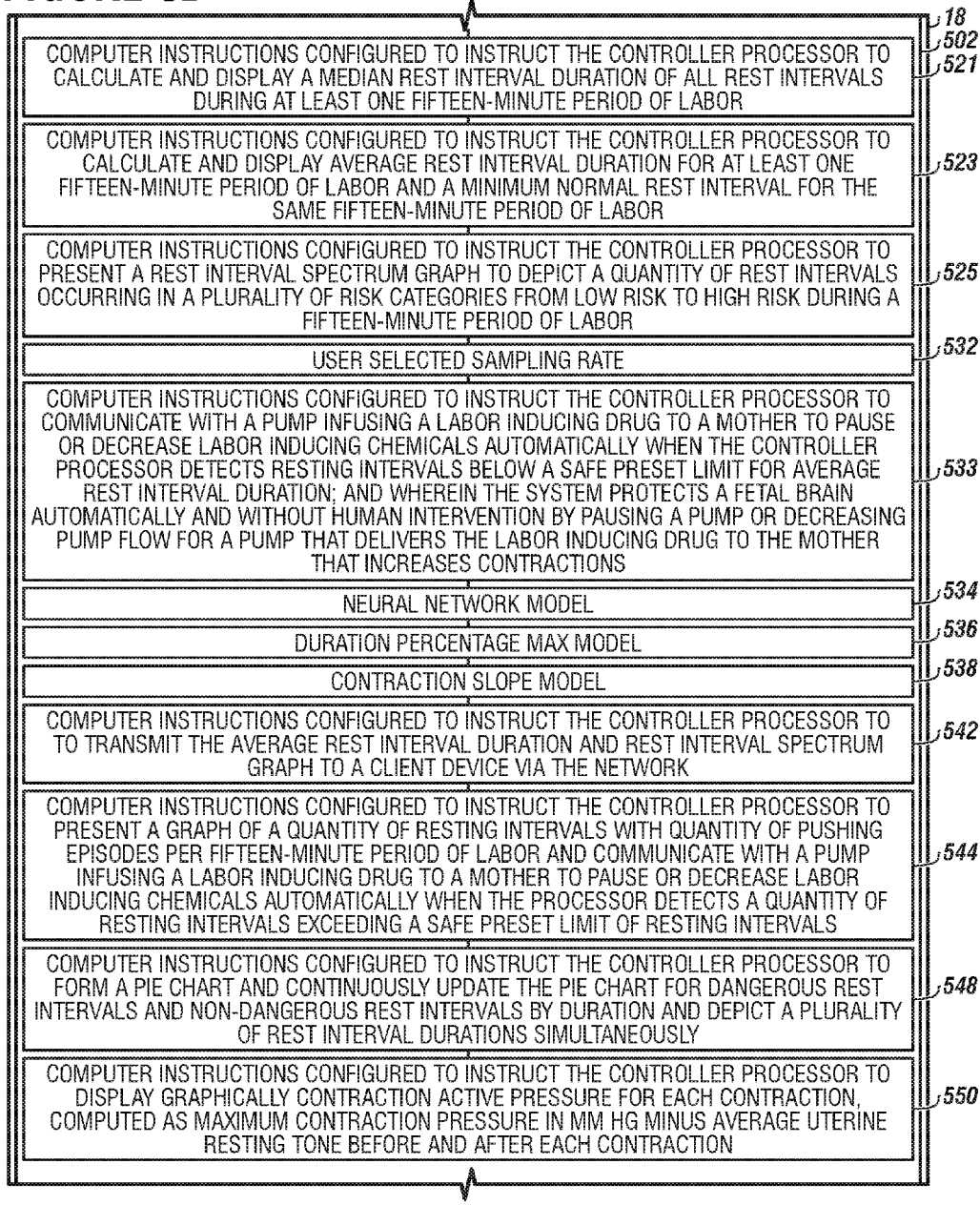
Figure 3C:
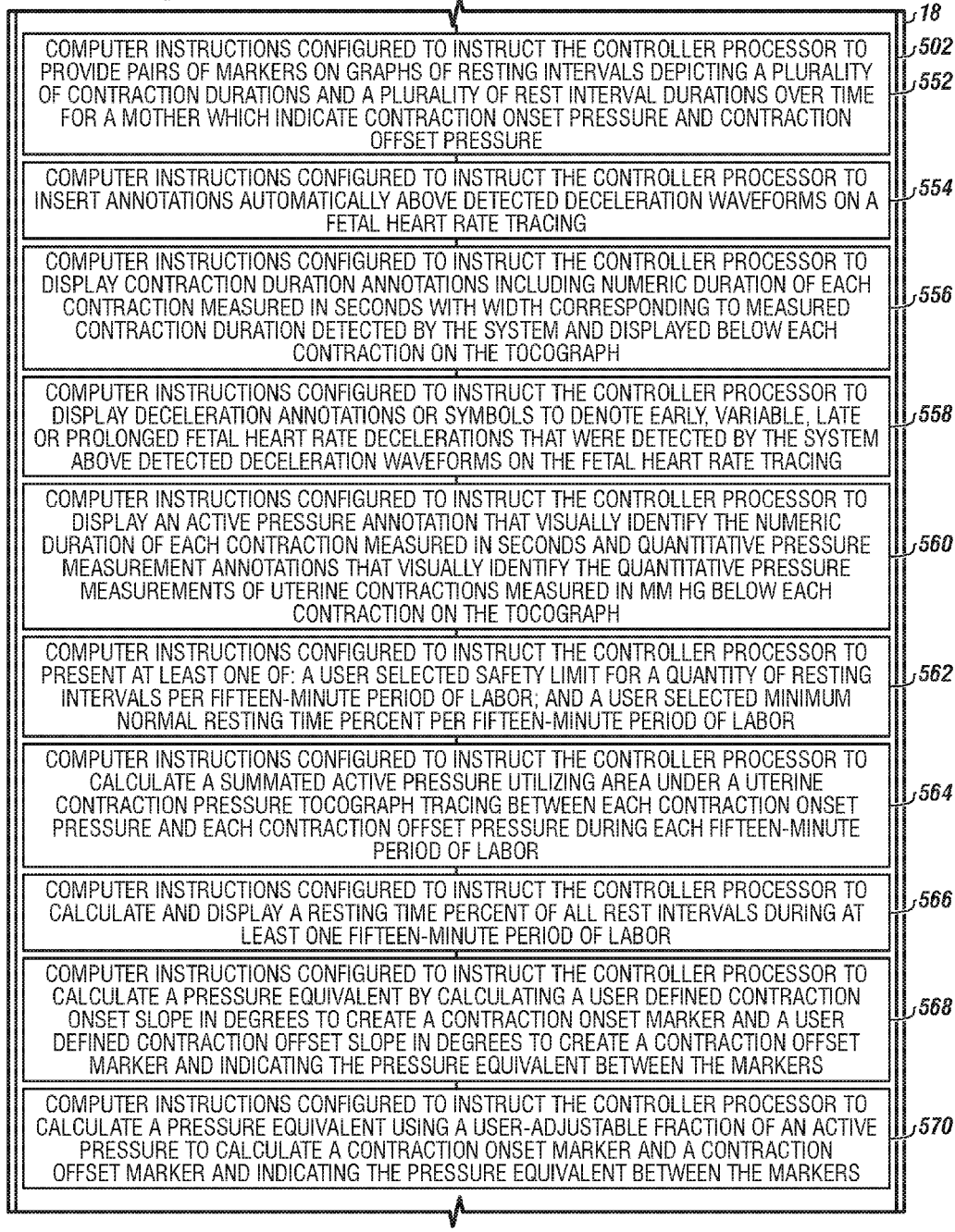
Figure 3D:
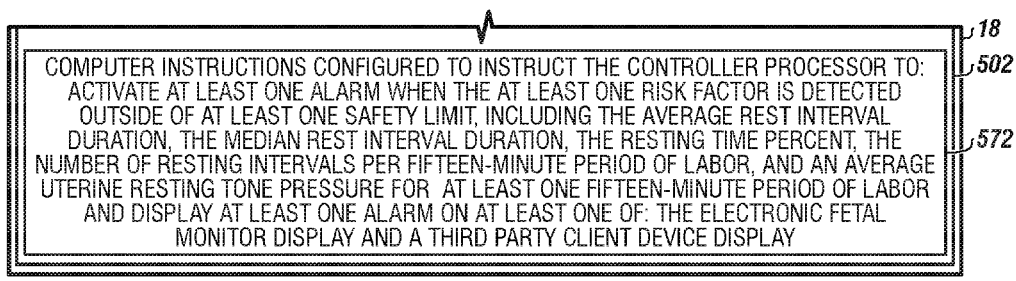

Turning now to the Figures, FIG. 1 is a diagram of an overview of the digital electronic fetal heart rate and uterine contraction monitoring system and FIG. 2 is a diagram of an electronic fetal monitor according to one or more embodiments.

The digital electronic fetal heart rate and uterine contraction monitoring system 8 can include an electronic fetal monitor 9 or "EFM".

The electronic fetal monitor 9 can display and printout units of pressure, which can include measures of uterine contraction pressure. When an intrauterine pressure monitor is used, calibrated pressure signals on a scale from 0 to 100 mm Hg can be displayed on a monitor screen or reviewed on a printout. The fetal heart rate can be graphed on a grid from 30 to 240 beats per minute, which can be from an internal (IUPC) monitor recording.

A contraction monitoring sensor 10 for measuring contractions can be secured to the mother 16, such as on the abdomen.

The contraction monitoring sensor 10 can transmit contraction pressure versus time data 34 to the electronic fetal monitor 9. In embodiments, the transmission of data can be sent via cables.

In embodiments, the contraction monitoring sensor 10 can be electronically connected or in wireless communication with the electronic fetal monitor 9.

A fetal heart rate sensor 11 for detecting fetal heart rate can be secured to the mother 16 or to the scalp of a fetus inside the mother. The fetal heart rate sensor 11 can be electronically connected to the electronic fetal monitor 9 for monitoring fetal heart rate versus time data 32.

The electronic fetal monitor 9 can have an electronic fetal monitor display 24, a printer 25, an electronic fetal monitor processor 20, and an electronic fetal monitor data storage 22. The electronic fetal monitor data storage 22 can be in communication with the electronic fetal monitor processor 20.

The electronic fetal monitor 9 can have a controller 18, which can be installed in the electronic fetal monitor 9. In embodiments, the controller can be a chip, which can electronically communicate to the electronic fetal monitor processor 20.

The controller 18 can be configured to receive detected fetal heart rate versus time data 32 from the fetal heart rate sensor 11, receive contraction pressure versus time data 34 from the contraction monitoring sensor 10, identify a contraction offset, also known as a contraction end time, identify a contraction on set, also known as a contraction start time, calculate each rest interval in units of time, such as in seconds, between contractions and save the rest intervals in units of time in the electronic fetal monitor data storage.

The controller 18 can compare rest intervals to a safe preset limit for rest intervals and calculate a median rest interval for each fifteen-minute period of labor.

The controller 18 can calculate average rest intervals for each fifteen-minute period of labor and present contraction durations and rest interval durations as a graph of median rest intervals and average rest intervals, such as in seconds, for each fifteen-minute period of labor to a client device 36 via a network 28.

In embodiments, the electronic fetal monitor processor 20 and the controller 18 can be in communication with the network 28.

The controller 18 can activate at least one alarm when at least one significant criteria of excessive uterine activity is detected outside of user-defined safety limits in order to assure adequate blood flow to the fetal brain and prevent intracranial ischemia.

The at least one alarm 26a can be displayed on the electronic fetal monitor display 24, the at least one alarm 26b can be displayed on a third party client device display 42 or both the electronic fetal monitor display and the third party client device display.

In embodiments, the at least one alarm can be displayed on at least one of the displays or on both displays simultaneously.

The at least one alarm can be an audio alarm, a visual alarm, a message alarm, such as an email, a text message or an audio message, or combinations thereof.

The at least one alarm can include updated graphs depicting risk trends to medical providers describing an event that triggered the system to detect risks or technical problems with labor.

In embodiments, the at least one alarm can be a flashing light, a large alarm symbol on the display, and another type of alarm, such as a discrete beeping which is different from the beeping associated with heart monitors.

In embodiments, the client device 36 can be connected to the network 28. The client device 36 can be a computer, a laptop, a cellular or smart phone, a tablet computer, a personal digital assistant, or combinations thereof. The client device can contain a third party processor with a third party data storage and have the ability to display graphs and provide bi-directional communication. The client device 36 can have a third party data input device 44, such as a keyboard.

In embodiments, the electronic fetal monitor 9 can communicate via the network 28 to a hospital medical records processor 100, which can enable the controller 18 to receive medical record data automatically from the hospital medical records processor 100 via the network 28 for use in presenting data on the mother 16 to a healthcare worker tending to the mother and for computational operations performed by the controller 18.

The electronic fetal monitor 9 can be in communication with a pump 46 for infusing a labor inducing chemical 29, such as oxytocin to the mother 16. The controller 18 in the electronic fetal monitor 9 can stop or decrease medication infusion when at least one alarm is activated.

In embodiments, the pump 46 can be in communication with the electronic fetal monitor 9 via cable 30 enabling further communication of pump operational conditions with the network 28 enabling remote monitoring of labor. In embodiments, the controller 18 can provide bi-directional communication with the pump 46.

In embodiments, the controller 18 can be in the electronic fetal monitor 9, the client device, or combinations thereof.

In embodiments, the digital electronic fetal heart rate and uterine contraction monitoring system 8 can include a maternal heart rate sensor 118 which can be attached to the mother 16, for detecting a maternal heart rate versus time data 33 and providing maternal heart rate versus time data to the electronic fetal monitor 9.

The maternal heart rate sensor 118 can be in wired communication or wireless communication with the electronic fetal monitor 9, which can further communicate with the controller 18.

The controller 18 can be configured to receive and display a maternal heart rate tracing 119 from the maternal heart rate sensor 118. The controller 18 can be configured to receive and display a fetal heart rate tracing 133 from the fetal heart rate sensor 11.

FIGS. 3A-3D depict the controller, controller processor, and data storage of the digital electronic fetal heart rate monitor.

The controller 18 can have a controller processor 301 and a controller data storage 502. The controller data storage 502 can instruct the controller processor 301 to perform various tasks using a plurality of computer instructions.

In embodiments, the controller 18 can contain, store or calculate the fetal heart rate versus time data 32, the maternal heart rate versus time data 33, the contraction pressure versus time data 34, and combinations thereof.

The controller data storage 502 can contain computer instructions 504 configured to instruct the controller processor to record fetal heart rate versus time data from the fetal heart rate sensor and display a fetal heart rate tracing.

The controller data storage 502 can contain computer instructions 506 configured to instruct the controller processor to record maternal heart rate versus time data from the maternal heart rate sensor and display a maternal heart rate tracing.

The controller data storage 502 can contain computer instructions 508 configured to instruct the controller processor to receive and store the fetal heart rate versus time data, the maternal heart rate versus time data, and the contraction pressure versus time data at a user selected sampling rate.

The controller data storage 502 can contain computer instructions 509 configured to detect, calculate and store an average contraction onset time, an average contraction offset time, an average contraction onset pressure, and an average contraction offset pressure utilizing at least one of: a neural network model for contraction onset and contraction offset, a duration percentage max model for contraction onset and contraction offset, and a contraction slope model for contraction onset and contraction offset.

In embodiments, the controller data storage 502 can contain the neural network model 534 for contraction onset and contraction offset, the duration percentage max model 536 for contraction onset and contraction offset, and the contraction slope model 538 for contraction onset and contraction offset.

The controller data storage 502 can contain computer instructions 511 configured to instruct the controller processor to detect and store active pressure of each detected contraction by subtracting average uterine resting tone pressure from a contraction peak pressure.

The controller data storage 502 can contain computer instructions 513 configured to instruct the controller processor to simultaneously compute, store, and display each measure of the duration of each resting interval in seconds utilizing a stored average contraction onset time and a stored average contraction offset time data both graphically and numerically.

The controller data storage 502 can contain computer instructions 515 configured to instruct the controller processor to display measures of the duration of each contraction in seconds with the pressure of each contraction measured on a mm Hg pressure scale.

The controller data storage 502 can contain computer instructions 517 configured to instruct the controller processor to detect, store and display associated with fetal heart rate tracing at least one of: an early fetal heart rate deceleration, variable fetal heart rate deceleration, late fetal heart rate deceleration and prolonged fetal heart rate deceleration by simultaneous analysis of the fetal heart rate tracing and uterine contraction pressure versus time in a tocograph tracing of uterine contraction patterns.

The controller data storage 502 can contain computer instructions 521 configured to instruct the controller processor to calculate and display a median rest interval duration of all rest intervals during at least one fifteen-minute period of labor.

The controller data storage 502 can contain computer instructions 523 configured to instruct the controller processor to calculate and display average rest interval duration for at least one fifteen-minute period of labor and a minimum normal rest interval for the same fifteen-minute period of labor.

The controller data storage 502 can contain computer instructions 525 configured to instruct the controller processor to present a rest interval spectrum graph to depict a quantity of rest intervals occurring in a plurality of risk categories from low risk to high risk during a fifteen-minute period of labor.

In embodiments, the controller data storage 502 can contain a user selected sampling rate 532. The user selected sampling rate 532 can be samples of the fetal heart rate versus time data, the maternal heart rate versus time data, and the contraction pressure versus time data selected by the user.

The controller data storage 502 can contain computer instructions 533 configured to instruct the controller processor to communicate with a pump infusing a labor inducing drug to a mother to pause or decrease labor inducing chemicals automatically when the controller processor detects resting intervals below a safe preset limit for average rest interval duration and wherein the system protects a fetal brain automatically and without human intervention by pausing the pump or decreasing a pump flow for the pump that delivers the labor inducing drug to the mother that increases contractions.

The controller data storage 502 can contain computer instructions 542 to instruct the controller processor to transmit the average rest interval duration and rest interval spectrum graph to a client device via the network.

The controller data storage 502 can contain computer instructions 544 configured to instruct the controller processor to present a graph of a quantity of resting intervals with quantity of pushing episodes per fifteen-minute period of labor and communicate with a pump infusing a labor inducing drug to a mother to pause or decrease labor inducing chemicals automatically when the processor detects a quantity of resting intervals exceeding a safe preset limit of resting intervals.

The controller data storage 502 can contain computer instructions 548 configured to instruct the controller processor to form a pie chart and continuously update the pie chart for dangerous rest intervals and non-dangerous rest intervals by duration and depict a plurality of rest interval durations simultaneously.

In embodiments, the controller data storage 502 can contain, form and record the pie chart 200, which can be continuously updated.

The controller data storage 502 can contain computer instructions 550 configured to instruct the controller processor to display graphically contraction active pressure for each contraction, computed as maximum contraction pressure in mm Hg minus average uterine resting tone before and after each contraction.

The controller data storage 502 can contain computer instructions 552 configured to instruct the controller processor to provide pairs of markers on graphs of resting intervals depicting a plurality of contraction durations and a plurality of rest interval durations over time for a mother, which indicate contraction onset pressure and contraction offset pressure.

The controller data storage 502 can contain computer instructions 554 configured to instruct the controller processor to insert annotations automatically above detected deceleration waveforms on a fetal heart rate tracing.

The controller data storage 502 can contain computer instructions 556 configured to display contraction duration annotations including numeric duration of each contraction measured in seconds displayed with width corresponding to measured contraction duration detected by the system and displayed below each contraction on the tocograph.

The controller data storage 502 can contain computer instructions 558 configured to instruct the controller processor to display deceleration annotations to denote early, variable, late or prolonged fetal heart rate decelerations that were detected by the system above detected deceleration waveforms on the fetal heart rate tracing.

The controller data storage 502 can contain computer instructions 560 configured to instruct the controller processor to display an active pressure annotation that visually identify the numeric duration of each contraction measured in seconds and quantitative pressure measurement annotations that visually identify the quantitative pressure measurements of uterine contractions measured in mm Hg below each contraction on the tocograph.

The controller data storage 502 can contain computer instructions 562 configured to instruct the controller processor to present at least one of: a user selected safety limit for a quantity of resting intervals per fifteen-minute period of labor, a user selected minimum normal resting time percent per fifteen-minute period of labor, a user selected minimum average rest interval duration per fifteen-minute period of labor, a user selected minimum median rest interval duration per fifteen-minute period of labor, and a user selected maximum average uterine resting tone per fifteen-minute period of labor.

The controller data storage 502 can contain computer instructions 564 configured to instruct the controller processor to calculate a summated active pressure utilizing area under a uterine contraction pressure tocograph tracing between each contraction onset pressure and each contraction offset pressure during each fifteen-minute period of labor.

The controller data storage 502 can contain computer instructions 566 configured to instruct the controller processor to calculate and display a resting time percent of all rest intervals during at least one fifteen-minute period of labor.

The controller data storage 502 can contain computer instructions 568 configured to instruct the controller processor to calculate a pressure equivalent by calculating: a user defined contraction onset slope in degrees to create a contraction onset marker and a user defined contraction offset slope in degrees to create a contraction offset marker and indicating the pressure equivalent between the markers.

The controller data storage 502 can contain computer instructions 570 configured to instruct the controller processor to calculate a pressure equivalent using: a user adjustable fraction of an active pressure to calculate a contraction onset marker and a contraction offset marker and indicating the pressure equivalent between the markers.

In embodiments, the user adjustable fraction of an active pressure can be 1 percent to 99 percent.

The controller data storage 502 can contain computer instructions 572 configured to instruct the controller processor to activate at least one alarm when the at least one risk factor is detected outside of at least one safety limit, including the average rest interval duration, the median rest interval duration, the resting time percent, the number of resting intervals per fifteen-minute period of labor, and an average uterine resting tone pressure for at least one fifteen-minute period of labor and display at least one alarm on at least one of: the electronic fetal monitor display and a third party client device display.

FIG. 4A depicts a fetal heart rate tracing 133 and maternal heart rate tracing 119 above a uterine contraction tracing during an eight-minute segment of labor for a normal baby showing rest interval duration annotations and contraction duration and active pressure annotations.

The cardiotocograph 206 is shown with an upper cardiograph panel 208 displaying the fetal heart rate tracing 133 and the maternal heart rate tracing 119.

The upper cardiograph panel 208 can display annotations "E", "V", "L" or "P" to respectively denote early, variable, late or prolonged fetal heart rate decelerations that were detected by the system. One of the annotations 212a is depicted as a "V".

In embodiments, the annotations can be displayed above detected deceleration waveforms on the fetal heart rate tracing 133.

The lower cardiograph panel 214 depicts uterine contraction pressure versus time in a tocograph tracing 221.

The system can display active pressure 216a, 216b, and 216c and contraction peak pressure 603a, 603b, and 603c. The cardiotocograph 206 also shows contraction peak pressure minus average uterine resting tone pressure 601a, 601b, and 601c.

Contraction onset time 230a, 230b, and 230c and the contraction offset time 232a and 232b are shown.

Contraction onset time 230a and 230b mark the end of each resting interval and contraction offset time 232a and 232b mark the beginning of each resting interval.

The measures of the duration of each resting interval 240a, 240b and 240c are shown, which can be depicted in seconds.

The measures of the duration of each contraction 242a, 242b, and 242c with the pressure of each contraction are shown, wherein the duration of each contraction can be depicted in seconds and the pressure of each contraction can be measured on a mm Hg pressure scale.

To provide a visual display of resting interval adequacy, the measure of the duration of each resting interval 240a, 240b, and 240c can be color coded using green to depict safe rest interval durations and red to depict unsafe resting interval durations.

An average contraction onset pressure 220a, 220b, and 220c and an average contraction offset pressure 222a and 222b are also depicted.

Figure 4B:
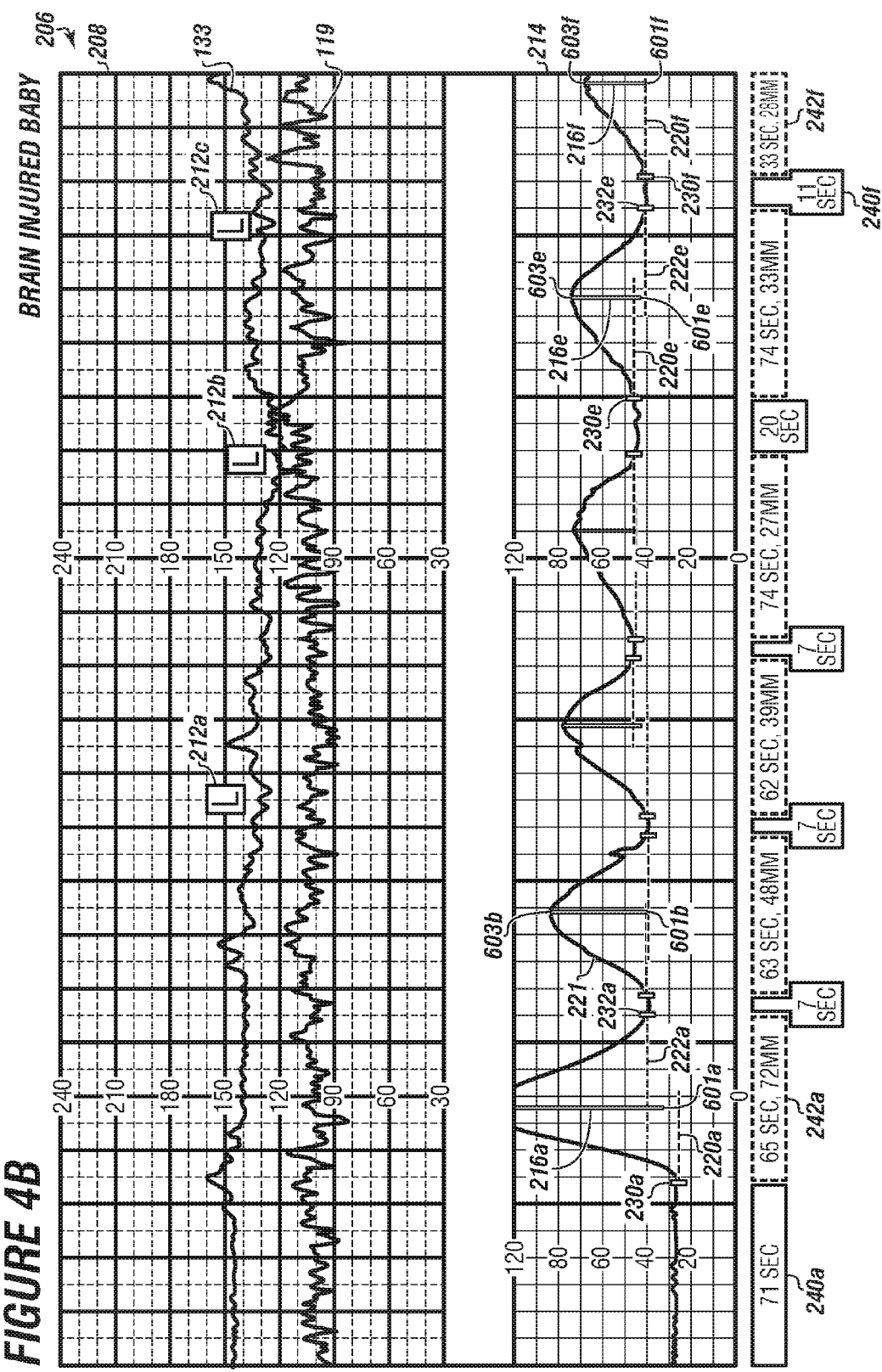
FIG. 4B depicts a fetal heart rate tracing and maternal heart rate tracing above a uterine contraction tracing during an eight-minute segment of labor for a brain injured baby.

FIG. 4B depicts a fetal heart rate tracing and maternal heart rate tracing above a uterine contraction tracing during an eight-minute segment of labor for a brain injured baby showing rest interval duration annotations and contraction duration and active pressure annotations.

The cardiotocograph 206 is shown with the upper cardiograph panel 208 displaying the fetal heart rate tracing 133 and the maternal heart rate tracing 119.

Annotations 212a, 212b, 212c are depicted as an "L" showing three late fetal heart rate decelerations detected by the system.

In embodiments, the annotations can be displayed above detected deceleration waveforms on the fetal heart rate tracing 133.

The lower cardiograph panel 214 depicts uterine contraction pressure versus time in the tocograph tracing 221.

The system displays active pressure 216a-216f. The active pressure depicts the strength of each contraction measured from the contraction peak to the average of pressure measured before and after each contraction.

Contraction peak pressures 603b-603f are also shown. The cardiotocograph 206 also shows contraction peak pressure minus average uterine resting tone pressure 601a-601f.

Contraction onset time 230a-230f, the contraction offset time 232a-232e, the average contraction onset pressure 220a-220f, the average contraction offset pressure 222a-222e, the measure of the duration of each resting interval 240a-240f, and the measures of the duration and pressure of each contraction 242a-242f are shown.

FIG. 4A and FIG. 4B reveal that each graph can enable any involved healthcare worker to view whether resting intervals are repetitively too short, representing increased risk trends.

FIG. 5A depicts a graph 500 for a normal baby depicting average and median rest interval durations during labor for a normal baby showing average and median rest interval durations in seconds during each fifteen-minute period of labor and user adjustable normal rest interval duration in seconds that are used for comparison.

The average rest interval durations 555 are shown in seconds. The median rest interval durations 557 are shown in seconds. The user adjustable minimum normal rest interval duration 559 is shown.

This graph shows that with the exception of five instances, nearly all the median and average rest interval durations during this normal labor were in a safe range, above the user adjustable minimum normal rest interval duration of 60 seconds.

In contrast, FIG. 5B depicts a graph 502 for a brain injured baby depicting average and median rest interval durations during labor for a brain injured baby showing that most median and average rest interval durations were below the user adjustable minimum normal rest interval duration of 60 seconds.

The average rest interval durations 555 and the median rest interval durations 557 are shown in seconds. The user adjustable minimum normal rest interval duration 559 is shown as 60 seconds.

This graph shows that only 5 of the 70 periods of labor depicted had an average rest interval duration exceeding 60 seconds.

This graph also shows that only 3 of the 70 periods of rest intervals depicted had a median rest interval duration in seconds exceeding the user-adjustable safety limit of 60 seconds.

The graph visually identifies to medical personnel that the majority of median and average resting interval durations were often near the 20 second range, representing a trend of increased risk to the fetal brain.

Each of the graphs described above or combinations thereof can be transmitted to the electronic fetal monitor display or the third party client device display.

The graphs when viewed by medical providers, in conjunction with the system's ability to automatically pause the pump can reduce risks of fetal brain damage.

Medical personnel can also factor in other elements, including but not limited to a weight of a mother, a presence of maternal diabetes, advanced fetal gestational age, a macrosomic estimated fetal weight, a cephalopelvic disproportion, a primigravida mother, a mother's medical history, an abnormal labor curve with protraction and/or arrest of cervical dilatation and/or fetal head descent as entered in the mother's medical record, and other selected criteria to determine whether to restart the pump or reconsider alternative treatment options for labor and delivery.

FIG. 6A depicts a graph 600 of resting time percent between contractions during each fifteen-minute period of labor as compared to a user adjustable minimum normal rest percent used for comparison for a normal baby.

The X-axis depicts each fifteen-minute period of labor.

A resting time percent 604 between uterine contractions is compared to a minimum normal rest percent 608. The minimum normal resting time percent is a user adjustable percentage. In this graph, the user adjusted the minimum normal resting time percent 608 to 50%.

The graph 600 created by the system displays 35 periods of labor for the mother. During the first half of labor, the resting time percent 604 was mostly above the minimum normal resting time percent 608.

The resting time percent was safely above the user adjustable minimum normal resting time percent 608 of 50% during most of the first half of this labor. Occasionally, during the last half of this normal labor, the resting time percent was slightly below the user selected minimum normal resting time percent of 50%. The user can readjust the minimum normal resting time percent to minimize alarm fatigue.

FIG. 6B depicts a graph 602 of resting time percent between contractions during each fifteen-minute period of labor as compared to a user adjustable minimum normal resting percent used for comparison for a brain injured baby.

The graph 602 for a brain injured baby is shown with the resting time percent 604 contrasted to the user adjustable minimum normal resting time percent 608, shown at 50%. The resting time percentage was substantially less than 50%, often as low as 20% during many periods of labor, reflecting numerous periods with increased risk for fetal brain injury.

In particular, the graph 602 shows that the resting time percentage 604 was below 20% during 11 periods of 70 periods of the labor with only one period of labor with a minimum normal resting time percent 608 as high as 50%.

Figure 7A:
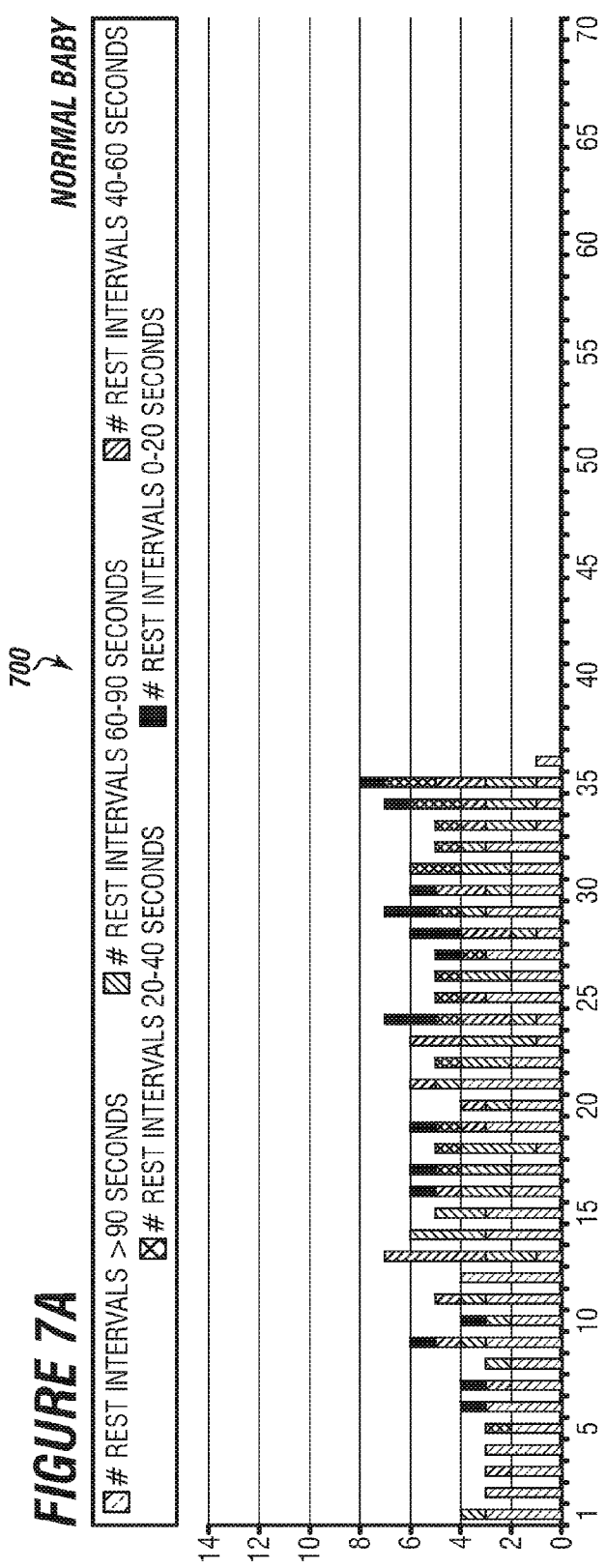
FIG. 7A shows 36 periods of labor for a normal baby depicting the number of very safe rest intervals, safe rest intervals, potentially inadequate rest intervals, potentially unsafe rest intervals and potentially dangerous rest intervals during each fifteen-minute period of labor.

FIG. 7A shows a graph of 36 periods of labor for a normal baby depicting the number of very safe rest intervals, safe rest intervals, potentially inadequate rest intervals, potentially unsafe rest intervals and potentially dangerous rest intervals for a mother.

The graph 700, shown as a stacked bar, depicts the details of labor for a normal baby showing the number of rest intervals that occurred during 36 periods of labor for a normal baby, while simultaneously depicting the relative duration of each rest interval.

The graph 700 depicts in period 1 for the normal baby that 3 very safe rest intervals (greater than 90 seconds), 1 safe rest interval (60-90 seconds), 0 potentially inadequate rest intervals, 0 unsafe rest intervals and 0 dangerous rest intervals (less than 20 seconds) occurred.

In period 35, 1 very safe rest interval (greater than 90 seconds), 2 safe rest intervals (60 to 90 seconds), 2 potentially inadequate rest intervals (40 to 60 seconds), 2 potentially unsafe rest intervals (20 to 40 seconds) and 1 potentially unsafe rest interval (1 to 20 seconds) occurred for this fetus that was birthed as a normal baby.

The system can produce a result that allows medical personnel to view the relative duration of rest intervals with a slight delay for processing to decide whether a fetus can tolerate a few short rest intervals, or whether a fetus needs timely intervention and alternative labor management to prevent trends of prolonged periods with repetitively inadequately short rest intervals that can lead to fetal brain injury.

The system can produce a color-coded stacked bar graph of a spectrum of rest interval durations that enables medical providers to visually see trends in the number of contractions and rest intervals as well as the number of rest intervals with safe versus unsafe duration as labor progresses.

The system can provide numeric and graphic objective measures to inform providers of risk trends and update graphs at the end of each fifteen-minute period of labor.

Figure 7B:
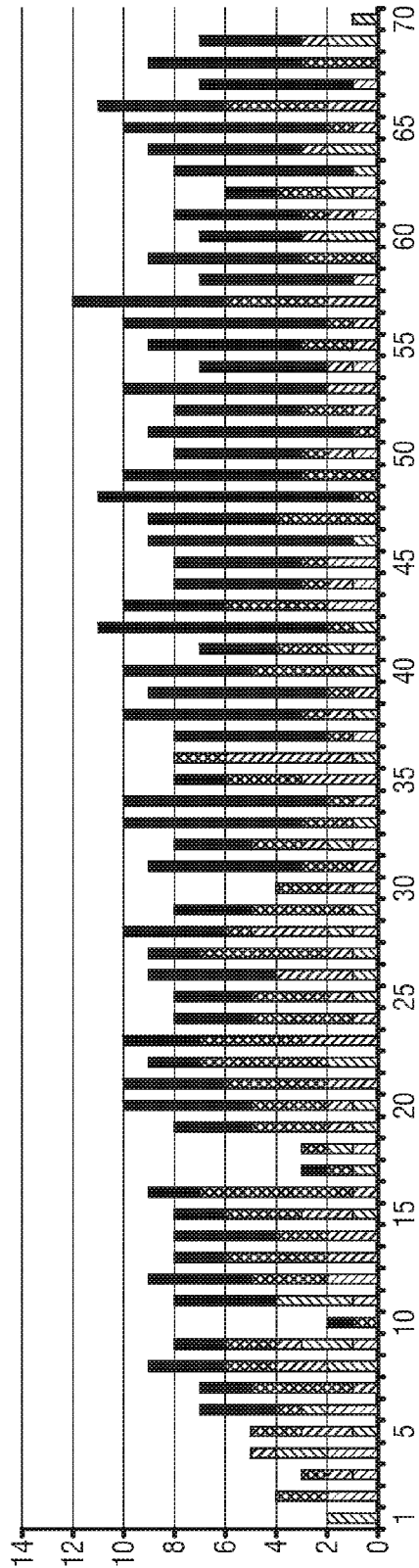
FIG. 7B shows 70 periods of labor for a brain injured baby depicting the number of very safe rest intervals, safe rest intervals, potentially inadequate rest intervals, potentially unsafe rest intervals and potentially dangerous rest intervals during each fifteen-minute period of labor.

FIG. 7B shows a graph 702 of 70 periods of labor for a brain injured baby depicting the number of very safe rest intervals, safe rest intervals, potentially inadequate rest intervals, potentially unsafe rest intervals and potentially dangerous rest intervals for a mother.

The graph 702 is shown as a stacked bar graph for a brain injured baby created by the system depicts the number of rest intervals during the last 70 periods of labor for a brain injured baby also depicting the relative duration of each rest interval.

The graph 702 can be scrolled to show the last 70 periods of labor for a labor that lasted over 105 periods for a brain injured baby.

The graph 702 shows in period 5 that 0 very safe rest intervals occurred, 1 safe rest interval occurred, 2 potentially inadequate rest intervals occurred, 2 unsafe rest intervals occurred and 0 dangerous rest intervals for the fetus occurred.

The graph 702 shows in period 48 that 0 very safe rest intervals occurred, 0 safe rest interval occurred, 0 potentially inadequate rest intervals occurred, 1 unsafe rest intervals occurred and 10 dangerous rest intervals (less than 20 seconds) occurred.

This embodiment depicts the number of rest intervals during each fifteen-minute period of labor as stacked bars, which can also be color coded, to reveal the proportion of intervals on a spectrum of safety.

In embodiments, very safe rest intervals for time intervals greater than 90 seconds can be colorized in green. Safe rest intervals for time intervals from 60 seconds to 90 seconds can be colorized in light green. Potentially inadequate rest intervals for time intervals from 40 seconds to 60 seconds can be colorized in yellow. Unsafe rest intervals for time intervals from 20 to 40 seconds can be colorized in orange. Potentially dangerous rest intervals for time intervals from 1 second to 20 seconds can be colorized in red.

In embodiments, the controller can present the number of rest intervals per fifteen-minute period of labor on the y-axis of the graph of FIG. 7A and FIG. 7B and transmit the graph for display on the electronic fetal monitor display, the third party client device display, or combinations thereof.

The third party client device display can enable a healthcare worker to clearly identify how many rest intervals are safe, potentially inadequate, potentially unsafe, and potentially dangerous during each fifteen-minute period of labor.

In embodiments, the graphs can depict periods of labor with unsafe conditions by displaying stacks of bars with an excessive proportion of yellow, orange and red bars and very few green bars, signifying that too many rest intervals are too short and too few have safe duration. In addition, the presence of more than 7 stacked bars depicts the risk factor of greater than seven contractions per fifteen-minute period of labor, a known risk for fetal brain injury.

The graphs can depict periods of labor with safe conditions by displaying up to seven stacked bars colored in green and light green making it easy to see on a monitor or the third party client device display that the fetus is not being subjected to repetitive, inadequately short resting intervals or excessively frequent contractions.

In embodiments, the digital electronic fetal heart rate and uterine contraction monitoring system can display colorized rest intervals that increase in brightness to highlight or act as a visual alarm that reveals when a dangerous condition exists.

In embodiments, the brightness can increase by a 10 percent level of brightness, but any brightness level can be used, or a chart of different brightness can be used. It can be expected that the highest level of brightness can indicate a preponderance of dangerous rest intervals from 1 second to 20 seconds with decreasing brightness as rest interval levels become progressively reassuring and safer.

In embodiments, the graphs can present a spectrum of rest intervals sorting the safer rest intervals on the bottom of the stack for each fifteen-minute period of labor and sequentially increasing in time intervals with the dangerous rest intervals on the top of each stack. The order of the rest intervals can be placed in a different sequence based upon user preference.

In embodiments, the system can create a display that is simple to understand, using color, position and brightness in order to display relative risks of adequate versus inadequate rest time between uterine contractions.

FIGS. 8A and 8B show deceleration graphs depicting some of the types of fetal heart rate decelerations as detected, measured, and recorded by the system during each fifteen-minute period of labor.

FIG. 8A shows a graph 800 of labor of a normal baby of fetal heart rate decelerations as detected by the system during each fifteen-minute period of labor.

The graph 800 of labor of a normal baby show two types of fetal heart rate decelerations as detected by the system during 36 fifteen-minute periods of labor.

Two early detections are shown during labor period 19 and two variable decelerations are shown in labor period 33.

FIG. 8B shows a graph 802 of labor of a brain injured baby of fetal heart rate decelerations as detected by the system during each fifteen-minute period of labor.

The graph 802 of labor of a brain injured baby shows that fetal heart rate decelerations were detected by the system during the majority the fifteen-minute periods of labor after labor period 20.

Most labor periods after labor period 20 showed late decelerations. Period 38 and period 69 each had 1 prolonged deceleration.

In embodiments, the graphs can be colorized.

FIG. 9A shows a graph 900 of labor of a normal baby depicting the number of resting intervals and the number of pushing episodes during each fifteen-minute period of labor as detected by the system.

The graph 900 shows the number of resting intervals, generally equivalent to a number of contractions, occurring during each fifteen-minute period of labor, as well as a number of maternal pushing episodes during each fifteen-minute period of labor.

The graph 900 shows the user selected safety limit 904 for a quantity of resting intervals per fifteen-minute period of labor.

The graph 900 shows the number of resting intervals 906 per fifteen-minute period of labor.

Also, a safety limit of seven resting intervals is depicted on the graph. The graph 900 depicts a normal labor with only one period of labor with more than seven resting intervals, corresponding to seven uterine contractions, per fifteen-minute period.

FIG. 9B shows a graph 902 of labor of a brain injured baby depicting the number of resting intervals every fifteen minutes and the number of pushing episodes as detected by the system.

The graph 902 shows a user selected safety limit 904 for a quantity of resting intervals per fifteen-minute period of labor.

The graph 902 shows the number of resting intervals 906, which can be generally equivalent to a number of contractions, occurring during each fifteen-minute period of labor and the number of maternal pushing episodes during each fifteen-minute period of labor are also shown.

A safety limit of seven resting intervals is also depicted the graph 902.

The graph 902 shows that 49 of the 70 periods of labor had more than seven resting intervals, corresponding to more than seven contractions during the labor period, a risk factor for fetal brain injury.

In general, the number of resting intervals can be equal to the number of uterine contractions, even though the system typically computes resting interval counts.

FIGS. 10A, 10B, 10C and 10D show graphs that report whether any risk factors occur during each fifteen-minute period of labor.

The system can continuously acquire and store rest interval duration, percent rest per period, number of rest intervals/contractions per period and uterine resting tone. At the conclusion of each fifteen-minute period, the system can calculate numerous parameters, including rest interval average duration, percent rest per period, total number of intervals per period and average uterine resting tone. These results can be compared to user adjustable safety limits chosen for each of these risk factors.

In these embodiments, the graphs display stacked bars to denote when any measured risk parameter has exceeded user adjustable preset limits during each period of labor.

Figure 10A:
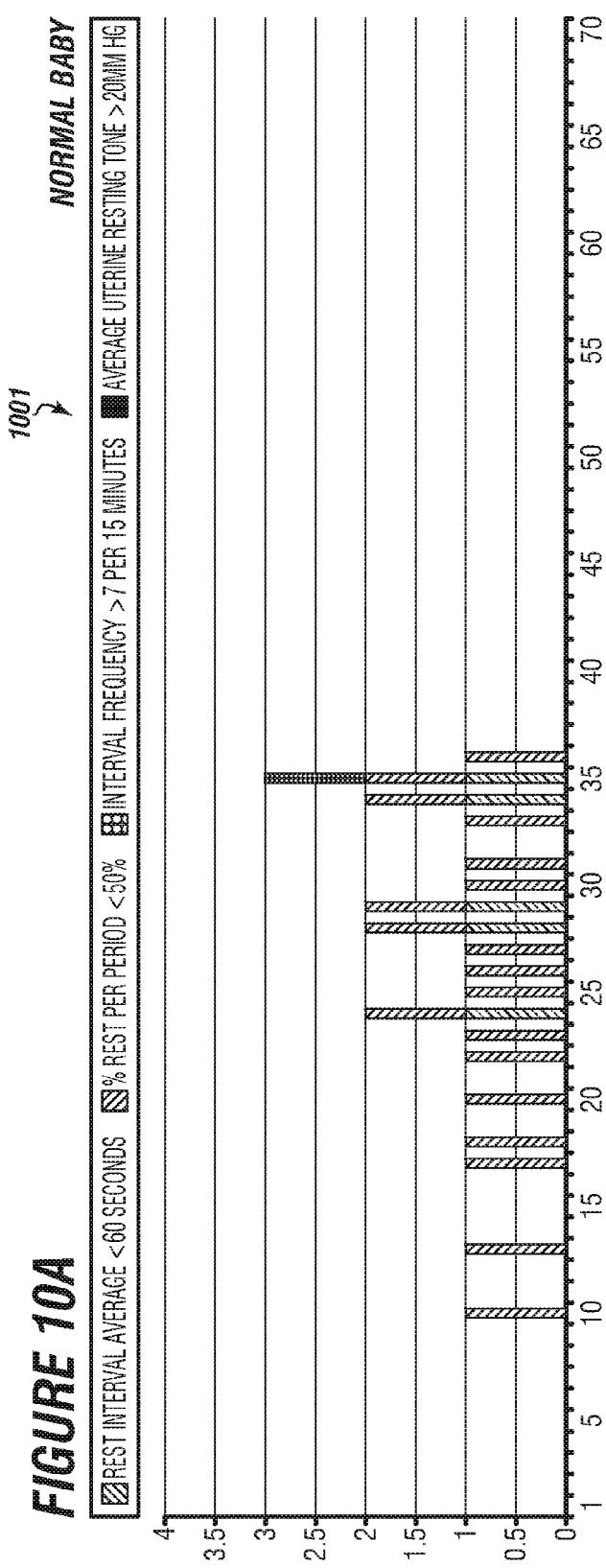
FIG. 10A shows a graph of a normal baby's labor depicting occurrence of excessive uterine activity parameters defined by an increased sensitivity definition of average rest interval duration (<60 seconds) and an increased sensitivity definition of percent resting time (<50%).

FIG. 10A shows a graph 1001 of a normal baby's labor depicting occurrence of any of four excessive uterine activity parameters during each fifteen-minute period of labor utilizing a user-defined increased sensitivity definition of rest intervals (<60 seconds) and an increased sensitivity definition of percent rest (<50%).

The graph 1001 displays risk factors exceeding normal safety limits for a normal baby as recorded during the labor of the normal baby.

In the graph 1001, user adjustable limits were conservatively set to detect relatively mild risks. These values were chosen as rest interval average <60 seconds, percent rest per period <50%, interval frequency >7 per fifteen-minute period of labor, and average uterine resting tone >20 mm Hg.

With these conservative settings, 19 periods of labor were identified as showing at least one risk. The conservative settings show 19 periods with percent rest per period <50%, 5 periods with rest interval average duration <60 seconds and one period with more than seven rest intervals per fifteen-minute period of labor. In this instance, providers can evaluate many aspects of the labor and determine that these user-defined risks may have been set too conservatively, resulting in alarm fatigue when the system reported slight deviations from optimal conditions too often although there were not clearly significant risks to the fetus.

FIG. 10B shows a graph 1002 of the normal baby's labor depicting occurrence of excessive uterine activity parameters defined by a decreased sensitivity definition of rest interval average duration (<50 seconds) and a decreased sensitivity definition of percent rest (<40%).

The graph 1002 displays risk factors exceeding normal safety limits for the normal baby as recorded during the labor of the normal baby.

The graph 1002 shows the results of risk factors to normal safety limits when some user adjustable settings were changed to less sensitive settings, including rest interval average <50 seconds, percent rest per period <40%, interval frequency >7 per fifteen-minute period of labor, and average uterine resting tone >20 mm Hg. With these less conservative settings, only 4 periods of labor were identified as showing some risks. For this mother's labor, these less conservative settings would have helped avoid alarm fatigue while still maintaining reasonable surveillance to detect trends of significant fetal risks due to excessive uterine activity.

The graph 1002 shows that period 24 had less than 40% rest per period and also had an average rest interval less than 50 seconds.

The graph 1002 shows that period 35 had more than seven rest intervals in the fifteen-minute period. However, this information of rarely occurring departures from safety limits can be unlikely to present significant fetal risks.

FIG. 10C shows a graph 1003 of a brain injured baby's labor depicting occurrence of excessive uterine activity parameters, defined by an increased sensitivity definition of rest intervals (<60 seconds) and an increased sensitivity definition of percent rest (<50%).

Graph 1003 depicts risk factors exceeding normal safety limits for a brain-injured baby as recorded during the labor of a brain-injured baby.

The graph 1003 shows that the labor in the brain-damaged baby had risks of excessive uterine activity during most periods of labor.

In this graph 1003 user adjustable limits were conservatively set to recognize relatively mild risks. These values were chosen as rest interval average <60 seconds, percent rest per period <50%, interval frequency >7 per fifteen-minute period of labor, and average uterine resting tone >20 mm Hg.

With these conservative settings, graph 1003 depicts that all but 4 of the last 70 periods of labor included risks or excessive uterine activity. Most of the labor periods had rest interval average duration <60 seconds. Most of the labor periods had percent rest per period <50%. Most of the labor periods had interval frequency >7 per fifteen-minute period of labor. In addition, average uterine resting tone was >20 mm Hg during 13 periods. Only 4 periods of labor were without risk factors present prior to the final labor period.

The graph 1003 depicts an average rest interval duration 555 was less than 60 seconds during all but five of the fifteen-minute periods of labor, percent rest per period 604 was less than 50% for 55 of 70 periods of labor, interval frequency was greater than seven per period during 52 of 70 labor periods and average uterine resting tone 1005 was >20 mm Hg in 16 of 70 periods of labor.

FIG. 10D shows a graph 1004 of the brain injured baby's labor depicting occurrence of excessive uterine activity parameters defined by a reduced sensitivity definition of rest interval average duration (<50 seconds) and a reduced sensitivity definition of percent rest per period (<40%), interval frequency >7 per fifteen-minute period of labor, and average uterine resting tone >20 mm Hg.

In graph 1004, user adjustable limits were less conservatively set than graph 1003 to avoid alarm fatigue while still recognizing substantial risks.

With these conservative settings, graph 1004 depicts that all but 6 of 70 periods of labor included risks or excessive uterine activity. 63 of 70 labor periods had a rest interval average <50 seconds, 52 of 70 had percent rest per period <40%, 50 of 70 had interval frequency >7 per fifteen-minute period of labor, and 13 of 70 had average uterine resting tone >20 mm Hg.

Graph 1004 shows that the labor in the brain-damaged baby had risks of excessive uterine activity during most periods of labor with only 6 periods of labor without risk factors present prior to the final labor period.

By using these less conservative user adjustable limits, Graph 1004 identified that user defined safety limits were exceeded in 6 of the 70 periods of labor. Comparison of FIG. 10C and FIG. 10D can demonstrate that using less conservative user-defined safety limits did not substantially impair the ability to detect trends of increased risks of excessive uterine activity.

Figure 11:
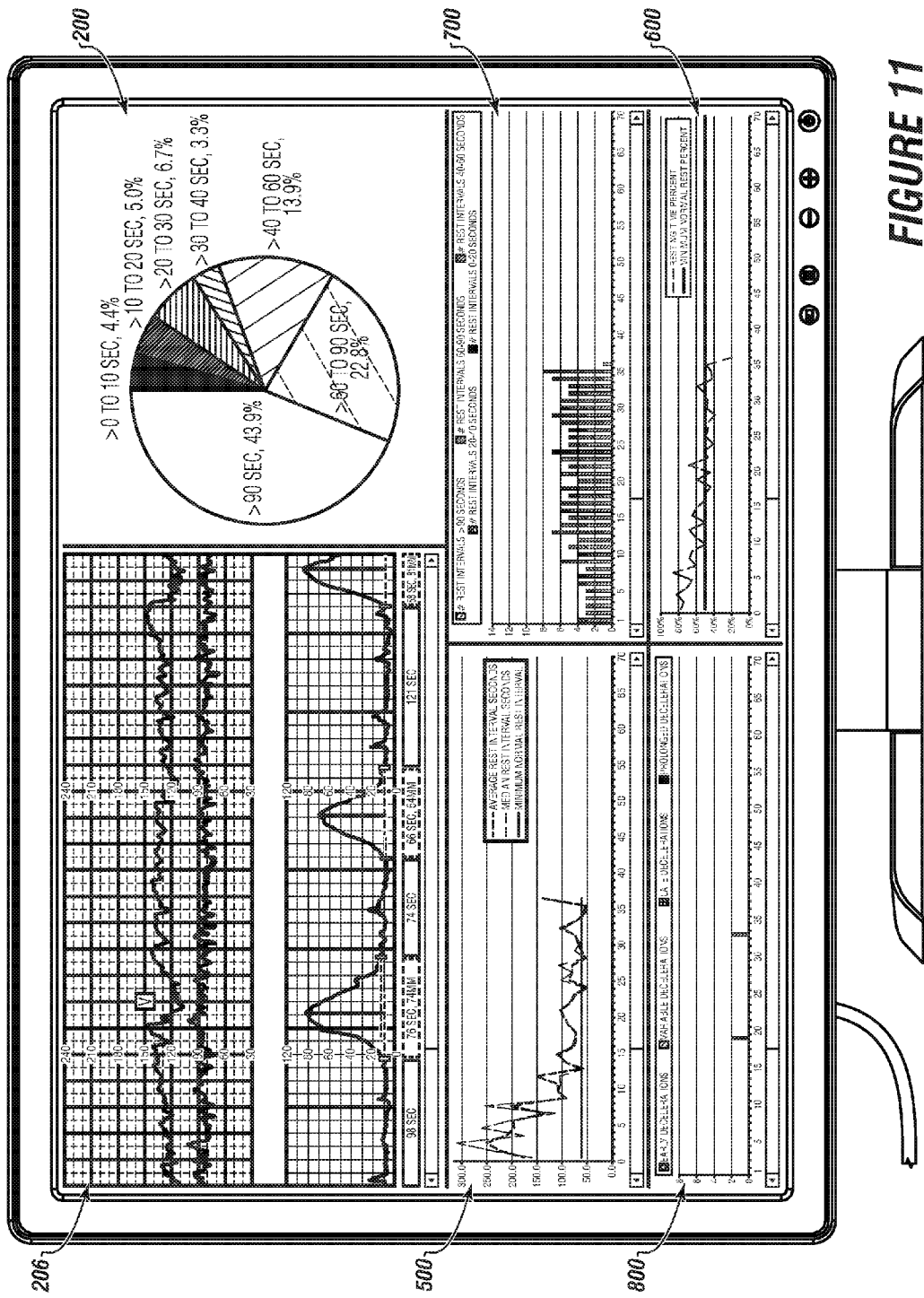
FIG. 11 depicts a display of a client device with multiple graphs created by the system.

FIG. 11 depicts a display of a client device with multiple graphs created by the system for a labor that produced a normal baby.

The display presents a cardiotocograph 206, which can be scrollable and annotated. The cardiotocograph 206 is shown above a graph of the number of rest intervals per labor period, which can be color-coded to depict rest interval durations.

The display can present a graph 500 of average and median rest intervals during labor for a normal baby.

The display can present a graph 800 of labor of a normal baby of fetal heart rate decelerations as detected by the system, such as having only two types of fetal heart rate decelerations during the period of labor which lasted 36 periods.

The display depicts one of many options used to display available data to allow providers to see current fetal monitoring conditions and trends of fetal monitoring conditions. In this example, several available graphs can be displayed simultaneously on computer monitors and personal data devices, such as laptops, tablet computers, cellular phones, and smart phones.

The system can generate a pie chart 200 to display seven categories that reflect rest interval duration during either a single period of labor or a user selected period of labor.

The pie chart 200 can be for any user selected periods of labor or a preset period of labor.

For example, the pie chart can show the most recent period of labor, trends during selected continuous periods of labor or the entire labor period prior to birthing the baby.

The pie chart can show as wedges, the percentage of rest intervals with average duration in the very safe range greater than 90 seconds, the safe range from 60 to 90 seconds, the potentially inadequate range from 40 to 60 seconds, the potentially unsafe range from 20 to 40 seconds, the unsafe range from 10 to 20 seconds and the potentially dangerous range of less than 10 seconds. In embodiments, the pie chart can be colorized.

The display shows a graph 700, shown as a stacked bar graph, similar to FIG. 7A, for a normal baby that depicts the number of rest intervals depicting the spectrum of duration from safe to unsafe range during 36 periods of labor.

In embodiments, the display can present a graph 600 of resting time percent between contractions during each fifteen-minute period of labor as compared to a user adjustable minimum normal rest percent used for comparison for a normal similar to FIG. 6A.

Figure 12:
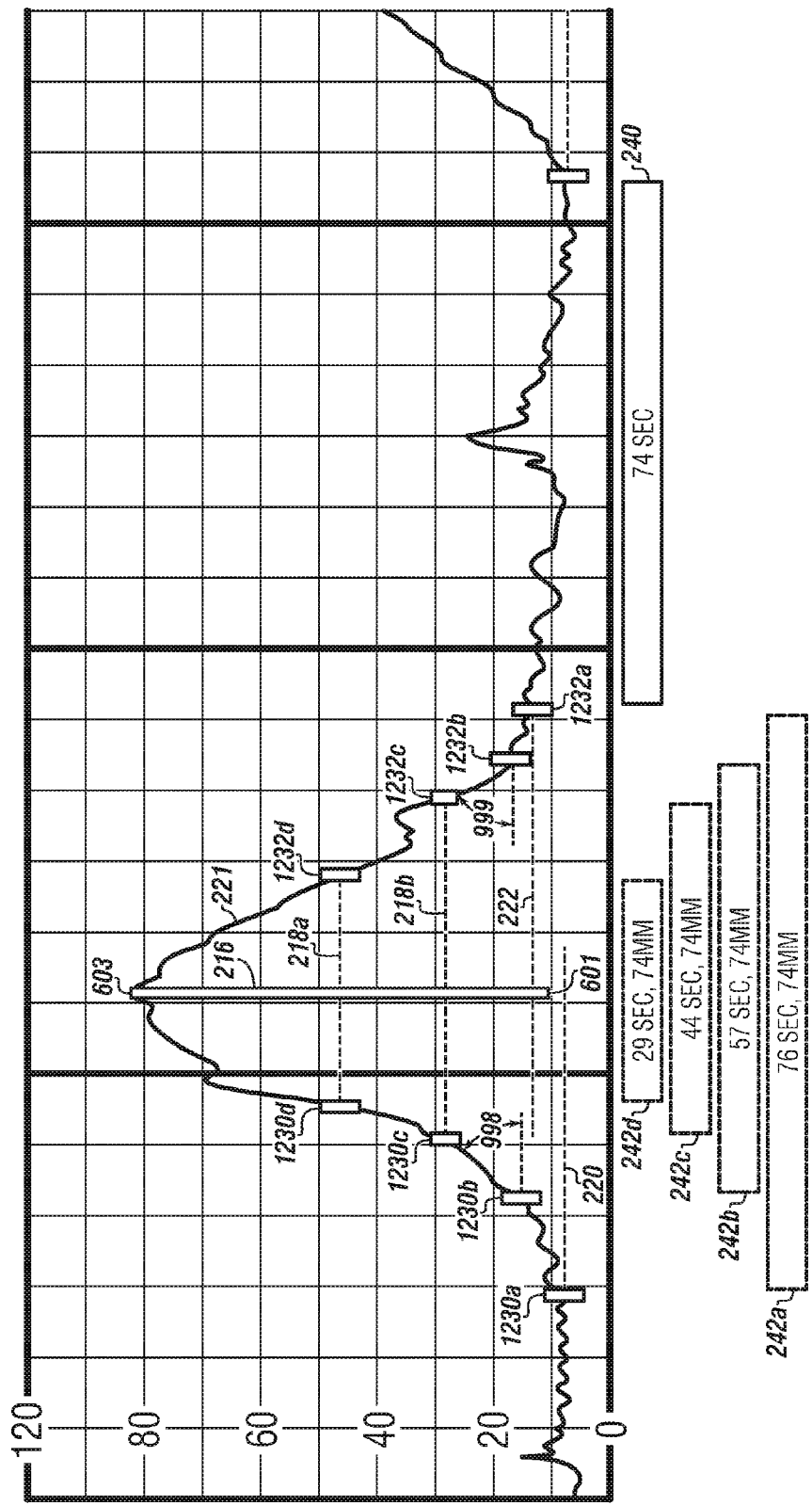
FIG. 12 depicts a graph using optional methods to determine contraction onset time and pressure and contraction offset time and pressure.
Figure 13:
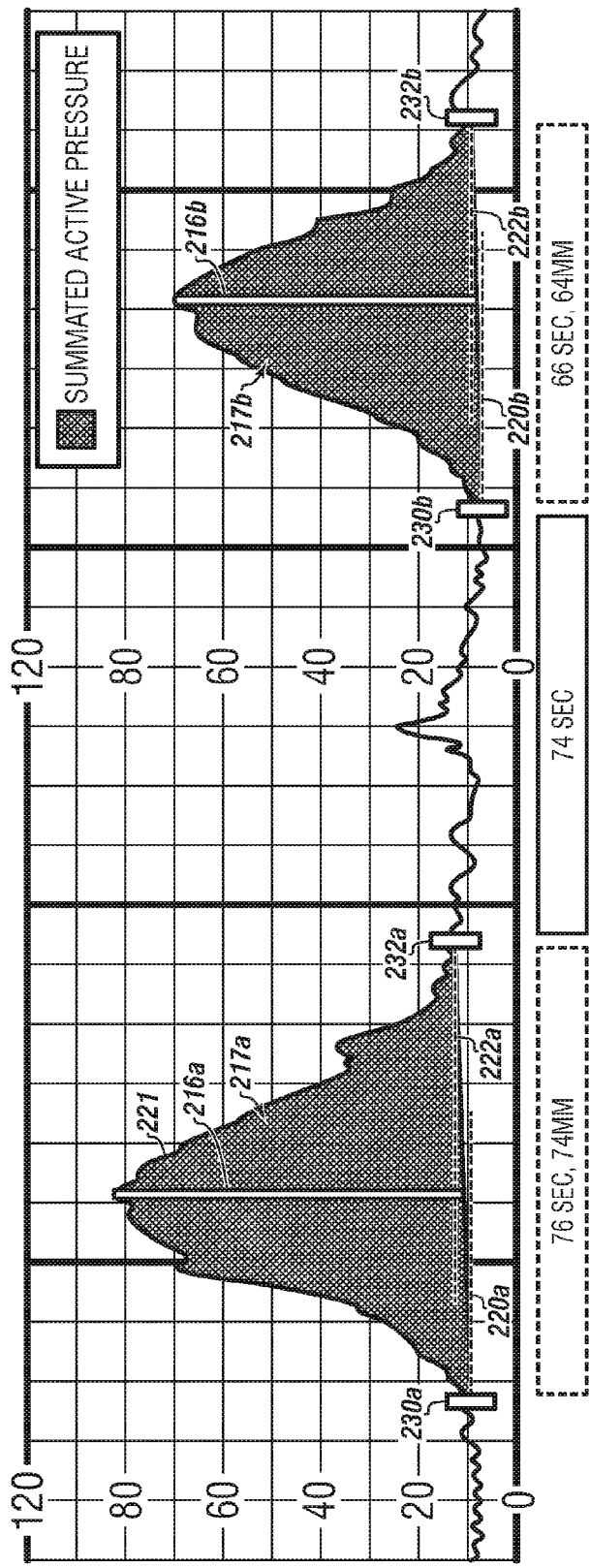
FIG. 13 depicts a graph of a pressure×duration area under a uterine contraction curve.

FIGS. 12 and 13 depict methods of marking contraction intervals and resting intervals to determine resting interval duration, a parameter that is important in determining risks for fetal brain injury.

A first method can use the neural network model for contraction onset and contraction offset. A second method can use the duration percentage max model for contraction onset and contraction offset. The third method can use the contraction slope model to detect contraction onset and contraction offset. A fourth method can use a user adjustable minimum pressure model.

The first method can determine contraction onset when the pressure baseline before contraction onset is essentially flat. Once there is any detectable increase in slope of the contraction curve, the contraction onset can be recognized. The contraction offset can be determined when the slope returns to an essentially flat baseline after the contraction while taking into consideration the noise of the baseline.

The second method is a user adjustable slope method. With the second method, the system detects contraction onset when the slope of the tocograph tracing 221 is significantly elevated to a user defined degree, which is shown in FIG. 12 as approximately 30 degrees to 45 degrees. The contraction offset can be marked when the slope falls below the user adjustable slope. This method avoids the need to count irrelevant tails of contractions on the tocograph tracing when the contraction pressure increases or decreases only slightly before or after the part of the contraction when contraction pressure is significantly elevated. This method can avoid over-interpreting resting intervals as too short because of very conservative inclusion of trivial pressure increases at the beginnings and ends of contractions.

The third method to detect timing of contraction onset and contraction offset that causes meaningful increased pressure upon the placenta and fetal head during a contraction is the user adjustable fraction method. The user adjustable fraction method can utilize user adjustable fractions of active pressure measures for each contraction. This model to allow users to focus on the portion of each contraction when contraction pressure is significantly elevated and potentially is dangerous to a fetus versus parts of contraction pressure that are only insignificantly elevated. FIG. 12 depicts user adjustable fractions, wherein user adjustable fraction 218a evaluates contraction duration when contraction pressure exceeds 50% of each contraction's active pressure and user adjustable fraction 218b evaluates contraction duration when contraction pressure exceeds 75% of each contraction's active pressure.

The fourth method to detect timing of contraction onset and contraction offset that causes meaningful increased pressure upon the placenta and fetal head during a contraction is a user adjustable minimum pressure model that evaluates only the portion of each contraction above a user adjustable minimum pressure for each contraction, which is shown in FIG. 14.

FIG. 12 depicts a graph using optional methods to determine contraction onset pressure and contraction offset pressure.

The slope method utilizes a user defined contraction onset slope 998 depicting the rate of increase in degrees of graphed pressure versus time can be used to create a contraction onset marker 1230b and use a user defined contraction offset slope 999 in degrees to create a contraction offset marker 1232b.

The user adjustable fraction method utilizes a user adjustable fraction 218a of each contraction's active pressure 216 (50%) to create a contraction onset marker 1230d and contraction offset marker 1232d or alternatively at a user adjustable fraction of (75%) 218b of an active pressure 216 to create a contraction onset marker 1230c and contraction offset marker 1232c. The user adjustable fraction can range from 1% to 100%. When the user adjustable fraction is set at 100%, the entire duration of each contraction is detected, as reflected by contraction onset marker 1230a and a contraction offset marker 1232a.

Average uterine resting tone pressure 601, contraction peak pressure 603, average contraction onset pressure 220 and average contraction offset pressure 222 are also shown.

Average uterine resting tone pressure 601 can be computed by averaging the average contraction onset pressure 220 and the average contraction offset pressure 222. The active pressure 216 for each contraction can be computed by subtracting the average uterine resting tone pressure 601 from the contraction peak pressure 603. The graph simultaneously depicts the measure of the duration of each resting interval 240 utilizing stored average contraction onset time and average contraction offset time data both graphically and numerically.

Annotations of the measures of the duration of each contraction 242a-242d, which can be shown in seconds and the pressure of each contraction measured on a mm Hg pressure scale can utilize methods of marking contraction intervals and resting intervals.

The neural network model for contraction onset and contraction offset detects the entire duration of each contraction 242a. The user-adjustable slope method detects a smaller duration of each contraction 242b. The user adjustable fraction method, 242c at 75% and 242d at 50%, detects the duration of the contraction chosen by the user to detect the portion of the uterine contraction that is associated with sufficiently high pressure that could cause increased risks for fetal hypoxia and ischemia.

FIG. 13 depicts a graph of a pressure×duration area under a uterine contraction curve.

The graph generated by the system shows calculated summated active pressures 217a and 217b. Each summated active pressure can be calculated by measuring the area under the curve for each uterine contraction using the uterine contraction pressure tocograph tracing 221, which are solely between the contraction onset pressure 230a and the contraction offset pressure 232a across each fifteen-minute periods of labor.

For the summated active pressure 217a, the active pressure 216a is used between contraction onset pressure 230a and contraction offset pressure 232a.

For the summated active pressure 217b, the active pressure 216b is used between contraction onset pressure 230b and contraction offset pressure 232b.

The horizontal dotted lines are calculated depicting an average contraction onset pressure 220a and 220b, and the horizontal dotted lines are calculated depicting an average contraction offset pressure 222a and 222b.

The measure of the duration of each resting interval is shown as 74 seconds, which is shown in the solid line box.

The measures of the duration and active pressure of each contraction is shown as 76 seconds and 74 mm Hg and 66 seconds and 64 mm Hg, which are shown in the dashed line boxes.

Summated active pressure can be determined by integrating the area under the curve for each contraction during each fifteen-minute period of labor or by multiplying the active pressure×contraction duration for each contraction during each fifteen-minute period of labor.

FIG. 14 depicts a graph using optional methods of timing onset and offset of contractions.

The fourth method to detect timing of contraction onset and contraction offset that causes meaningful increased pressure upon the placenta and fetal head during a contraction is a user adjustable minimum pressure model that evaluates only the portion of each contraction above a user adjustable minimum pressure for each contraction in a tocograph tracing 221.

The graph depicts the fraction of contraction duration when contraction pressure exceeds the user adjustable minimum pressure 1401*a* of 20 mm Hg to create a contraction onset marker 1230*a* and a contraction offset marker 1232*a*. When the user adjustable minimum pressure 1401*b* is set at 25 mm Hg the contraction duration when contraction pressure exceeds 25 mm Hg is determined by a contraction onset marker 1230*b* and a contraction offset marker 1232*b*.

The active pressure 216 for each contraction can be computed by subtracting the average uterine resting tone pressure 601 from the contraction peak pressure 603.

Figure 15A:
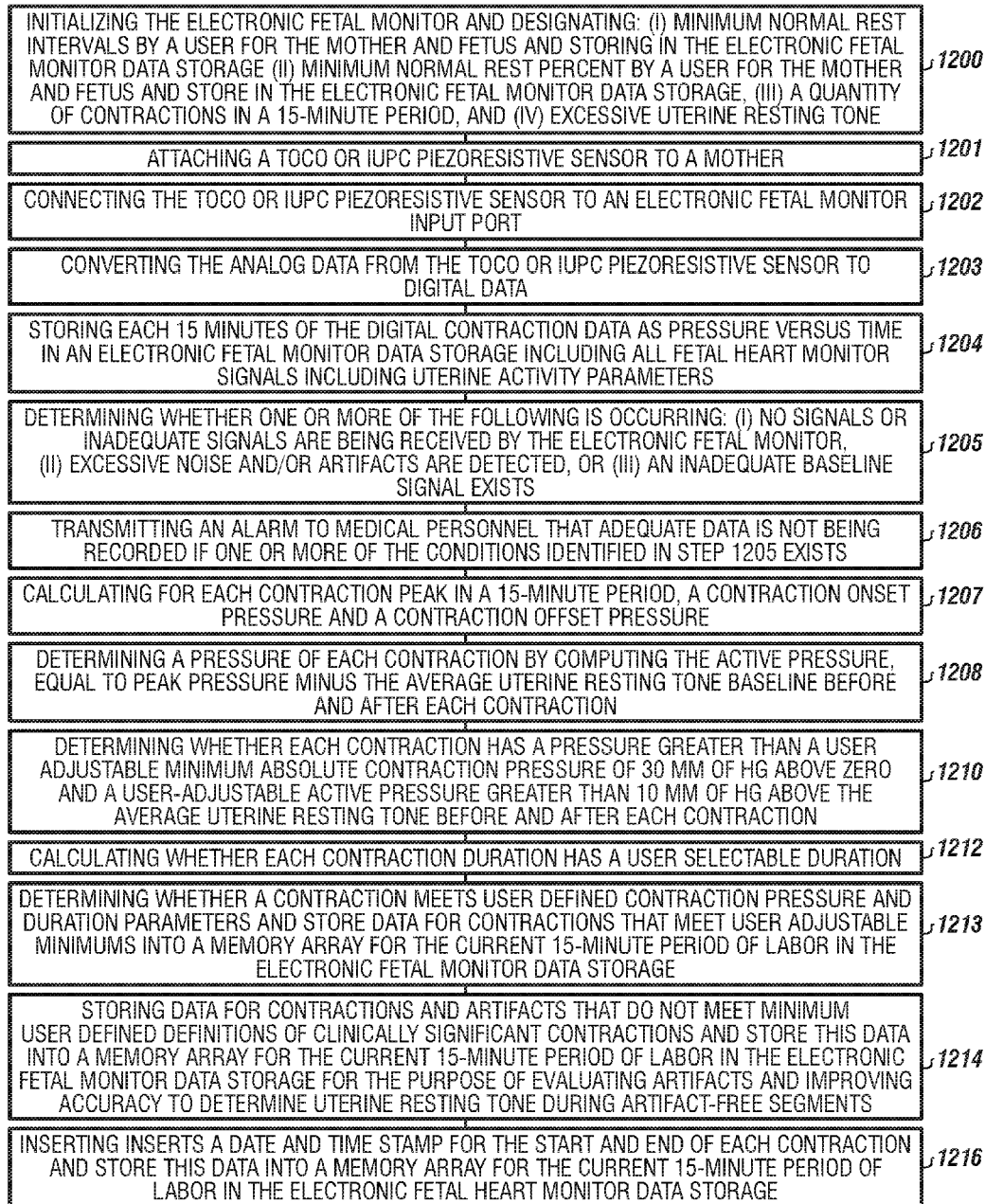
FIGS. 15A-15B display an exemplary sequence of steps according to the system as it relates to analysis of uterine contractions.
Figure 15B:
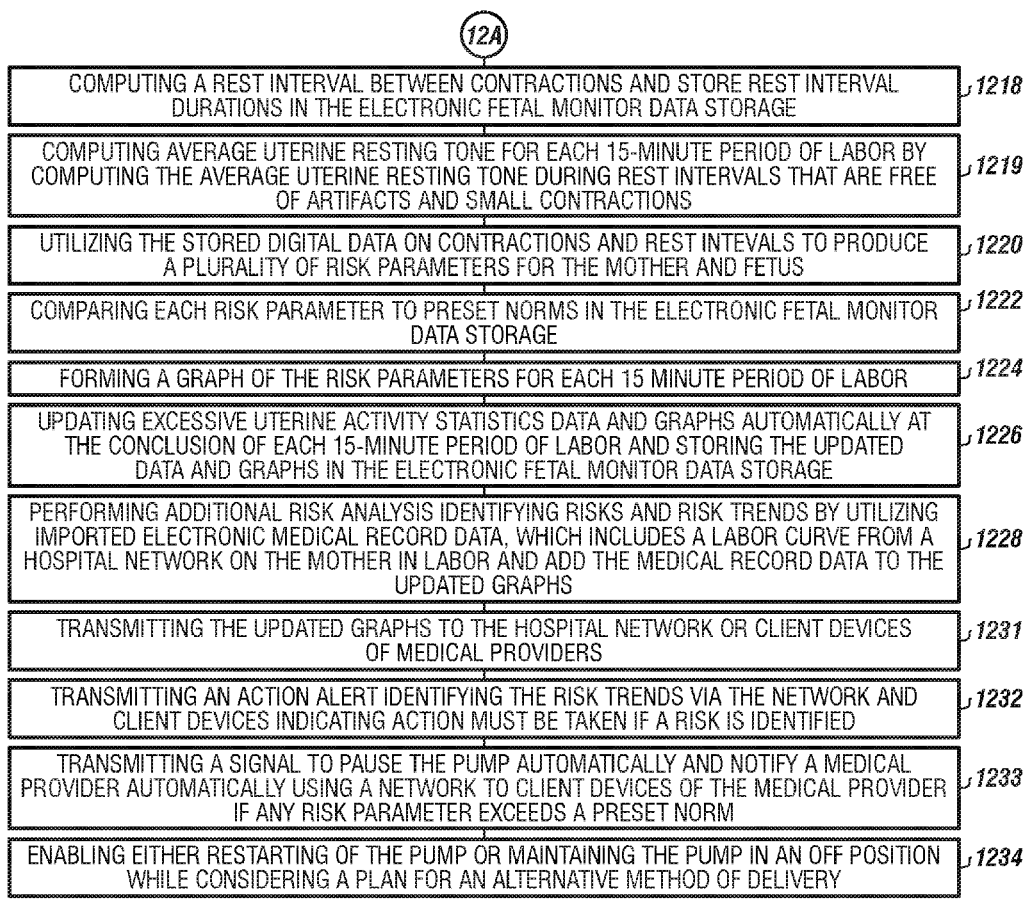

FIGS. 15A-15B display an exemplary sequence of steps according to the system as it relates to analysis of uterine contractions.

The sequence of steps can include initializing the electronic fetal monitor and designating: (i) minimum normal rest intervals by a user for the mother and fetus and storing in electronic fetal monitor data storage, (ii) minimum normal rest percent by a user for the mother and fetus and store in the electronic fetal monitor data storage, (iii) a quantity of contractions in a fifteen-minute period of labor, and (iv) excessive uterine resting tone, as shown in box 1200.

In embodiments, the quantity of contractions is generally seven and excessive uterine resting tone is in excess of 20 millimeters of Hg, the minimum normal rest percent can be 50%, and the average resting intervals can be 60 seconds.

The sequence of steps can include attaching a TOCO or IUPC piezoresistive sensor to the mother, as shown in box 1201.

The sequence of steps can include connecting the TOCO or IUPC piezoresistive sensor to an electronic fetal monitor input port, as shown in box 1202.

The sequence of steps can include converting the analog data from the TOCO or IUPC piezoresistive sensor to digital data, as shown in box 1203.

The sequence of steps can include storing each 15 minutes of the digital contraction data as pressure versus time in an electronic fetal monitor data storage including all fetal heart monitor signals including uterine activity parameters, as shown in box 1204.

The sequence of steps can include determining whether one or more of the following is occurring: (i) no signals or inadequate signals are being received by the electronic fetal monitor, (ii) excessive noise and/or artifacts are detected, or (iii) an inadequate baseline signal exists, as shown in box 1205.

The determination of the above step can be done via continuous monitoring.

The sequence of steps can include transmitting an alarm to medical personnel that adequate data is not being recorded if one or more of the conditions identified in step 1205 exists, as shown in box 1206.

The sequence of steps can include calculating for each contraction peak in a fifteen-minute period, a contraction onset pressure and a contraction offset pressure, as shown in box 1207.

The sequence of steps can include determining a pressure of each contraction by computing the active pressure, equal to peak pressure minus the average uterine resting tone baseline before and after each contraction, as shown in box 1208.

The sequence of steps can include determining whether each contraction has a pressure greater than a user adjustable minimum absolute contraction pressure of 30 mm of Hg above zero and a user-adjustable active pressure greater than 10 mm of Hg above the average uterine resting tone before and after each contraction, as show in box 1210.

The sequence of steps can include calculating whether each contraction duration has a user selectable duration, as shown in box 1212.

For example, the user selectable duration can be greater than 20 seconds in duration.

The sequence of steps can include determining whether a contraction meets user defined contraction pressure and duration parameters and store data for contractions that meet user adjustable minimums into a memory array for the current fifteen-minute period of labor in the electronic fetal monitor data storage, as shown in box 1213.

The sequence of steps can include storing data for contractions and artifacts that do not meet minimum user defined definitions of clinically significant contractions and store this data into a memory array for the current fifteen-minute period of labor in the electronic fetal monitor data storage for the purpose of evaluating artifacts and improving accuracy to determine uterine resting tone during artifact-free segments, as shown in box 1214.

The sequence of steps can include inserting a date and time stamp for the start and end of each contraction and store this data into a memory array for the current fifteen-minute period of labor in the electronic fetal monitor data storage, as shown in box 1216.

The sequence of steps can include computing a rest interval between contractions and store rest interval durations in the electronic fetal monitor data storage, as shown in box 1218.

The sequence of steps can include computing average uterine resting tone for each fifteen-minute period of labor by computing the average uterine resting tone during rest intervals that are free of artifacts and small contractions, as shown in box 1219.

The sequence of steps can include utilizing the stored digital data on contractions and rest intervals to produce a plurality of risk parameters for the mother and fetus, as shown in box 1220.

The risk parameters can include but is not limited to average rest interval duration in seconds, median rest interval duration in seconds, percent resting during each fifteen-minute period of labor, the frequency of rest intervals per fifteen-minute period of labor, the number of episodes of pushing per fifteen-minute period of labor and the average uterine resting tone during each fifteen-minute period of labor.

The sequence of steps can include comparing each risk parameter to preset norms in the electronic fetal monitor data storage, as shown in box 1222.

The sequence of steps can include forming a graph of the risk parameters for each fifteen-minute period of labor, as shown in box 1224.

The sequence of steps can include updating excessive uterine activity statistics data and graphs automatically at the conclusion of each fifteen-minute period of labor and storing the updated data and graphs in the electronic fetal monitor data storage, as shown in box 1226.

The sequence of steps can include performing additional risk analysis identifying risks and risk trends by utilizing imported electronic medical record data, which includes a labor curve from a hospital network on the mother in labor and add the medical record data to the updated graphs, as shown in box 1228.

The sequence of steps can include transmitting the updated graphs to the hospital network or client devices of medical providers, as shown in box 1231.

The sequence of steps can include transmitting an action alert identifying the risk trends via the network and client devices indicating action must be taken if a risk is identified, as shown in box 1232.

The sequence of steps can include transmitting a signal to pause the pump automatically and notify a medical provider automatically using a network to client devices of the medical provider if any risk parameter exceeds a preset norm, as shown in box 1233.

The sequence of steps can include restarting the pump or maintaining the pump in an off position while considering a plan for an alternative method of delivery, as shown in box 1234.

Alternative methods of delivery can include continuing to pause the pump and determining the prospects for safe, continued labor versus performing a Cesarean section.

FIG. 16 depicts an exemplary sequence of steps according to the system as it relates to analysis of fetal heart rate decelerations.

The sequence of steps can include attaching an ultrasound transducer or fetal scalp electrode sensor to the fetus to detect fetal heart rate, as shown in box 1300.

The sequence of steps can include transmitting analog contraction pressure data signals by cable from the fetal scalp electrode sensor or ultrasound transducer to an electronic fetal monitor, as shown in box 1302.

The sequence of steps can include receiving and storing the fetal heart rate data signals in the electronic fetal monitor data storage, as shown in box 1304.

The sequence of steps can include plotting a graph of fetal heart rate versus time and transmitting the graph to a printer, a network, client devices in communication with the network or combinations thereof, as shown in box 1306.

The sequence of steps can include performing a deceleration waveform analysis to detect early, variable, late, and prolonged fetal heart rate decelerations during each fifteen-minute period of labor, as shown in box 1308.

The sequence of steps can include adding deceleration waveform analysis annotations to the graph of fetal heart rate versus time, as shown in box 1310.

The sequence of steps can include storing each number and type of deceleration occurring during each fifteen-minute period of labor, as shown in box 1312.

The sequence of steps can include plotting the number of early, variable, late, and prolonged fetal heart rate decelerations occurring in each fifteen-minute period of labor and add the decelerations to the updated fetal graphs, as shown in box 1314.

The sequence of steps can include pushing the updated fetal graphs to the network, as shown in box 1316.

While these embodiments have been described with emphasis on the embodiments, it should be understood that within the scope of the appended claims, the embodiments might be practiced other than as specifically described herein.

What is claimed is:

1. A digital electronic fetal heart rate and uterine contraction monitoring system comprising:

a an electronic fetal monitor with an electronic fetal monitor processor, an electronic fetal monitor data storage, and an electronic fetal monitor display connected to the electronic fetal monitor processor, wherein the electronic fetal monitor processor is in further communication with a network;

b a contraction monitoring sensor for sensing uterine contraction pressure over time from a mother, wherein the contraction monitoring sensor is adapted to be secured to the mother and in communication with the electronic fetal monitor;

c a fetal heart rate sensor for sensing fetal heart rate over time from a fetus, wherein the fetal heart rate sensor is in communication with the electronic fetal monitor;

d a maternal heart rate sensor for sensing maternal heart rate over time from the mother, wherein the maternal heart rate sensor is in communication with the electronic fetal monitor; and e a controller comprising a controller processor and a controller data storage in communication with the electronic fetal monitor, the controller data storage having stored therein computer instructions that, when executed by the controller processor, causes the controller processor to:

i receive the sensed fetal heart rate from the fetal heart rate sensor, record and store the sensed fetal heart rate as fetal heart rate versus time data at a user selected sampling rate, and display the fetal heart rate versus time data as a fetal heart rate tracing;

ii receive the sensed maternal heart rate from the maternal heart rate sensor, record and store the sensed maternal heart rate as maternal heart rate versus time data at a user selected sampling rate, and display the maternal heart rate versus time data as a maternal heart rate tracing;

iii receive the sensed uterine contraction pressure from the contraction monitoring sensor, and record and store the sensed uterine contraction pressure as contraction pressure versus time data at a user selected sampling rate;

iv utilize the contraction pressure versus time data to detect, calculate and store a contraction onset time for each contraction, a contraction offset time for each contraction, an average contraction onset pressure, and an average contraction offset pressure utilizing at least one of: a neural network model for contraction onset and contraction offset, a duration percentage max model for contraction onset and contraction offset, a contraction slope model for contraction onset and contraction offset, and a user adjustable minimum pressure model that evaluates only a portion of each contraction above a user adjustable minimum pressure for each contraction;

v detect and store an active pressure of each detected contraction of the contraction pressure versus time data by subtracting an average uterine resting tone pressure from a contraction peak pressure;

vi compute, store, and display each measure of each resting interval duration in seconds utilizing a stored contraction onset time for a respective contraction and a stored contraction offset time for an immediately previous contraction, both graphically and numerically;

vii calculate and display a graph of an average rest interval duration for at least one fifteen-minute period of labor and a minimum normal rest interval for the same fifteen-minute period of labor;

viii present a rest interval spectrum graph to depict a quantity of rest intervals occurring in a plurality of risk categories from low risk to high risk during the at least one fifteen-minute period of labor;

ix transmit data and the graph depicting the average rest interval duration and the rest interval spectrum graph to a client device via the network; and x control a pump infusing a labor inducing drug to the mother to pause or decrease infusion of the labor inducing drug automatically when the controller processor detects resting intervals below a preset limit for the average rest interval duration, and wherein the digital electronic fetal heart rate and uterine contraction monitoring system protects a fetal brain automatically and without human intervention by pausing the pump or decreasing a pump flow for the pump that delivers the labor inducing drug to the mother that increases contractions.

2. The digital electronic fetal heart rate and uterine contraction monitoring system of claim 1, wherein the plurality of risk categories are discrete ranges of rest intervals comprising: very safe rest intervals for time intervals greater than 90 seconds, safe rest intervals for time intervals from 60 seconds to 90 seconds, potentially inadequate rest intervals for time intervals from 40 seconds to 60 seconds, unsafe rest intervals for time intervals from 20 seconds to 40 seconds if repetitive, and potentially dangerous rest intervals for time intervals from 1 second to 20 seconds if repetitive.

3. The digital electronic fetal heart rate and uterine contraction monitoring system of claim 2, wherein different risk categories of the plurality of risk categories are graphically differentiable in the rest interval spectrum graph by using different colors or different brightnesses.

4. The digital electronic fetal heart rate and uterine contraction monitoring system of claim 1, wherein the preset limit for the average rest interval duration is changeable using at least one risk factor associated with the mother and/or the fetus, the risk factors consisting of:
  a the mother's weight;
  b a presence of maternal diabetes;
  c an advanced fetal gestational age;
  d a macrosomic estimated fetal weight;
  e a cephalopelvic disproportion;
  f whether the mother is a primigravida;
  g the mother's medical history; and
  h a measured abnormal labor curve with protraction, arrest or both protraction and arrest of cervical dilatation, fetal head descent or both cervical dilatation and fetal head descent.

5. The digital electronic fetal heart rate and uterine contraction monitoring system of claim 1, wherein the computer instructions, when executed by the controller processor, further cause the controller processor to:
  a present a graph of a quantity of resting intervals with quantity of pushing episodes per fifteen-minute period of labor;
  b activate at least one alarm when at least one risk factor is detected outside of at least one safety limit, including the average rest interval duration, a median rest interval duration, resting time percent, the number of resting intervals per fifteen-minute period of labor, and an average uterine resting tone pressure for at least one fifteen-minute period of labor; and
  c control the pump infusing the labor inducing drug to the mother to pause or decrease the labor inducing chemicals automatically when the controller processor detects when the at least one risk factor is outside of the at least one safety limit.

6. The digital electronic fetal heart rate and uterine contraction monitoring system of claim 1, wherein the computer instructions, when executed by the controller processor, further cause the controller processor to detect, store and display, associated with fetal heart rate tracing, at least one of: an early fetal heart rate deceleration, a variable fetal heart rate deceleration, a late fetal heart rate deceleration and a prolonged fetal heart rate deceleration by simultaneous analysis of the fetal heart rate tracing and uterine contraction pressure versus time in a tocograph tracing of uterine contraction patterns.

7. The digital electronic fetal heart rate and uterine contraction monitoring system of claim 1, wherein the contraction monitoring sensor is at least one of:
  a a tocodynamometer adapted to be secured to the mother; and
  b an intrauterine pressure catheter adapted to be secured to the mother and connected to a pressure transducer to measure strength and duration of a contraction for the mother.

8. The digital electronic fetal heart rate and uterine contraction monitoring system of claim 1, wherein the fetal heart rate sensor is at least one of:
  a an ultrasound sensor adapted to be attached to the mother for monitoring a fetal heart rate; and
  b a fetal scalp electrode adapted to be attached to a fetal scalp for monitoring the fetal heart rate.

9. The digital electronic fetal heart rate and uterine contraction monitoring system of claim 1, wherein the computer instructions, when executed by the controller processor, further cause the controller processor to form and display a pie chart and continuously update the pie chart for dangerous rest intervals and non-dangerous rest intervals by duration and depict a plurality of rest interval durations simultaneously.

10. The digital electronic fetal heart rate and uterine contraction monitoring system of claim 3, wherein the different colors are different shades of primary and secondary colors to indicate very safe rest intervals, safe rest intervals, potentially inadequate rest intervals, inadequate rest intervals and potentially unsafe rest intervals for the fetus when these are repetitive.

11. The digital electronic fetal heart rate and uterine contraction monitoring system of claim 1, wherein the computer instructions, when executed by the controller processor, further cause the controller processor to display, graphically, contraction active pressure for each contraction, computed as maximum contraction pressure in mm Hg minus the average uterine resting tone pressure before and after each contraction.

12. The digital electronic fetal heart rate and uterine contraction monitoring system of claim 1, wherein the computer instructions, when executed by the controller processor, further cause the controller processor to provide pairs of markers on graphs of resting intervals depicting a plurality of contraction durations and a plurality of rest interval durations over time for the mother which indicate the average contraction onset pressure and the average contraction offset pressure.

13. The digital electronic fetal heart rate and uterine contraction monitoring system of claim 1, wherein the computer instructions, when executed by the controller processor, further cause the controller processor to insert annotations automatically above detected deceleration waveforms on the fetal heart rate tracing.

14. The digital electronic fetal heart rate and uterine contraction monitoring system of claim 1, wherein the comprises computer instructions, when executed by the controller processor, further cause the controller processor to display measurements of each contraction duration in seconds with measurements of each contraction pressure on a mm Hg pressure scale.

15. The digital electronic fetal heart rate and uterine contraction monitoring system of claim 6, wherein the computer instructions, when executed by the controller processor, further cause the controller processor to:
   a display contraction duration annotations including numeric duration of each contraction measured in seconds displayed with width corresponding to measured contraction duration detected by the digital electronic fetal heart rate and uterine contraction monitoring system and displayed below each contraction on the tocograph;
   b display deceleration annotations or symbols to denote early, variable, late or prolonged fetal heart rate decelerations, detected by the digital electronic fetal heart rate and uterine contraction monitoring system, above detected deceleration waveforms on the fetal heart rate tracing; and
   c display, below each contraction on the tocography, a contraction duration annotation and an active pressure annotation that visually identify both a numeric duration of each contraction measured in seconds and a quantitative pressure measurement of active pressure of each contraction measured in mm Hg.

16. The digital electronic fetal heart rate and uterine contraction monitoring system of claim 1, wherein the computer instructions, when executed by the controller processor, further cause the controller to:
   a detect risk trends describing a risk/problem event
   b upon detection of the risk trends, trigger detection of risks or technical problems of the digital electronic fetal heart rate and uterine contraction monitoring system; and
   c administer at least one alarm comprising:
      i at least one of: an audio alarm, a visual alarm, and a message alarm, and
      ii a graph depicting the risk trends to medical providers describing the risk/problem event.

17. The digital electronic fetal heart rate and uterine contraction monitoring system of claim 1, wherein the computer instructions, when executed by the controller processor, further cause the controller processor to present at least one of:
   a a user selected safety limit for a quantity of resting intervals per fifteen-minute period of labor;
   b a user selected minimum normal resting time percent per fifteen-minute period of labor;
   c a user selected minimum average rest interval duration per fifteen-minute period of labor;
   d a user selected minimum median rest interval duration per fifteen-minute period of labor; and
   e a user selected maximum average uterine resting tone pressure per fifteen-minute period of labor.

18. The digital electronic fetal heart rate and uterine contraction monitoring system of claim 6, wherein the computer instructions are further configured to cause the controller processor to calculate a summated active pressure utilizing area under a tocograph tracing of uterine contraction patterns between each contraction onset pressure and each contraction offset pressure during each fifteen-minute period of labor.

19. The digital electronic fetal heart rate and uterine contraction monitoring system of claim 5, wherein the computer instructions, when executed by the controller processor, further cause the controller processor to calculate and display a resting time percent of all rest intervals during the at least one fifteen-minute period of labor and computer instructions configured to instruct the controller processor to calculate and display a median rest interval duration and an average rest interval duration of all rest intervals during the at least one fifteen-minute period of labor.

20. The digital electronic fetal heart rate and uterine contraction monitoring system of claim 1, wherein the computer instructions, when executed by the controller processor, further cause the controller processor calculate a pressure equivalent by calculating:
   a a user defined contraction onset slope in degrees to create a contraction onset marker;
   b a user defined contraction offset slope in degrees to create a contraction offset marker; and
   c indicating the pressure equivalent between the contraction onset marker and the contraction offset marker.

21. The digital electronic fetal heart rate and uterine contraction monitoring system of claim 18, wherein the computer instructions, when executed by the controller processor, further cause the controller processor to detect the summated active pressure during portions of uterine contractions when risks of increased pressure are elevated by using a user adjustable fraction of the active pressure to calculate the summated active pressure by measuring the area under the curve for each contraction during each fifteen-minute period of labor.

22. The digital electronic fetal heart rate and uterine contraction monitoring system of claim 5, wherein the computer instructions, when executed by the controller processor, further cause the controller processor to display the at least one alarm on at least one of: the electronic fetal monitor display and a third party client device display.

* * * * *